(12) United States Patent
Trieu et al.

(10) Patent No.: US 7,204,851 B2
(45) Date of Patent: Apr. 17, 2007

(54) METHOD AND APPARATUS FOR DELIVERING AN INTERVERTEBRAL DISC IMPLANT

(75) Inventors: Hai H. Trieu, Cordova, TN (US); Jeff R. Justis, Gulf Breeze, FL (US); Roy Lim, Memphis, TN (US)

(73) Assignee: SDGI Holdings, Inc., Wilmington, DE (US)

( * ) Notice: Subject to any disclaimer, the term of this patent is extended or adjusted under 35 U.S.C. 154(b) by 185 days.

(21) Appl. No.: 10/717,687

(22) Filed: Nov. 20, 2003

(65) Prior Publication Data

US 2004/0117019 A1 Jun. 17, 2004

Related U.S. Application Data

(63) Continuation-in-part of application No. 10/459,630, filed on Jun. 11, 2003, now abandoned, which is a continuation-in-part of application No. 09/943,441, filed on Aug. 30, 2001, now abandoned, which is a continuation-in-part of application No. 09/650,525, filed on Aug. 30, 2000, now Pat. No. 6,620,196.

(51) Int. Cl.
*A61F 2/44* (2006.01)
*A61B 17/58* (2006.01)

(52) U.S. Cl. .............................. 623/17.11; 623/17.16; 606/99

(58) Field of Classification Search ............. 623/17.11, 623/17.12, 17.15, 17.16; 606/105, 57, 198, 606/90, 104, 60, 61, 63, 99
See application file for complete search history.

(56) References Cited

U.S. PATENT DOCUMENTS 3,486,505 A * 12/1969 Morrison ..................... 606/90

| | | |
|---|---|---|
| 3,867,728 A | 2/1975 | Stubstad et al. |
| 3,875,595 A | 4/1975 | Froning |
| 4,202,055 A | 5/1980 | Reiner et al. |
| 4,283,799 A | 8/1981 | Pratt, Jr. et al. |
| 4,349,921 A | 9/1982 | Kuntz |
| 4,428,082 A | 1/1984 | Naficy |
| 4,454,612 A | 6/1984 | McDaniel et al. |

(Continued)

FOREIGN PATENT DOCUMENTS

EP 0700 671 A1 3/1996

(Continued)

*Primary Examiner*—Alvin J. Stewart
(74) *Attorney, Agent, or Firm*—Woodard, Emhardt, Moriarty, McNett & Henry LLP

(57) ABSTRACT

A method for implanting a prosthetic spinal disc nucleus in an intervertebral disc nucleus space generally includes: (a) making a hole in the annulus of a disc, with the hole having an undilated size that is smaller than the cross-sectional size of a folded prosthetic disc nucleus; (b) using an implant instrument to dilate the hole in the disc annulus; (c) using the implant instrument to pass a straightened prosthetic disc nucleus through the dilated hole and into the disc nucleus space; (d) withdrawing the implant instrument and allowing the hole in the disc annulus to return to a size smaller that its dilated size; and (e) causing or allowing the prosthetic disc nucleus to assume a folded configuration with a cross-sectional size that is larger than its straightened size. A device for use in the method is also disclosed.

38 Claims, 23 Drawing Sheets

U.S. PATENT DOCUMENTS

| | | | |
|---|---|---|---|
| 4,545,374 A * | 10/1985 | Jacobson | 606/61 |
| 4,663,358 A | 5/1987 | Hyon et al. | |
| 4,772,287 A | 9/1988 | Ray et al. | |
| 4,863,477 A | 9/1989 | Monson | |
| 4,904,260 A | 2/1990 | Ray et al. | |
| 4,911,718 A | 3/1990 | Lee et al. | |
| 4,917,704 A | 4/1990 | Frey et al. | |
| 5,002,576 A | 3/1991 | Fuhrmann et al. | |
| 5,020,519 A * | 6/1991 | Hayes et al. | 606/237 |
| 5,035,716 A | 7/1991 | Downey | |
| 5,047,055 A | 9/1991 | Bao et al. | |
| 5,071,437 A | 12/1991 | Steffee | |
| 5,108,438 A | 4/1992 | Stone | |
| 5,147,646 A | 9/1992 | Graham | |
| 5,171,280 A * | 12/1992 | Baumgartner | 623/17.12 |
| 5,192,326 A * | 3/1993 | Bao et al. | 623/17.12 |
| 5,306,307 A | 4/1994 | Senter et al. | |
| 5,306,308 A | 4/1994 | Gross et al. | |
| 5,320,644 A | 6/1994 | Baumgartner | |
| 5,431,658 A * | 7/1995 | Moskovich | 606/99 |
| 5,443,727 A | 8/1995 | Gagnon | |
| 5,534,028 A | 7/1996 | Bao et al. | |
| 5,534,030 A | 7/1996 | Navarro et al. | |
| 5,545,229 A | 8/1996 | Parsons et al. | |
| 5,549,679 A | 8/1996 | Kuslich | |
| 5,562,736 A | 10/1996 | Ray et al. | |
| 5,571,189 A * | 11/1996 | Kuslich | 623/17.12 |
| 5,645,597 A * | 7/1997 | Krapiva | 606/61 |
| 5,674,294 A | 10/1997 | Bainville et al. | |
| 5,674,295 A | 10/1997 | Ray et al. | |
| 5,674,296 A | 10/1997 | Bryan et al. | |
| 5,676,698 A | 10/1997 | Janzen et al. | |
| 5,702,454 A | 12/1997 | Baumgartner | |
| 5,716,416 A | 2/1998 | Lin | |
| 5,755,797 A * | 5/1998 | Baumgartner | 623/17.16 |
| 5,800,549 A | 9/1998 | Bao et al. | |
| 5,824,093 A | 10/1998 | Ray et al. | |
| 5,863,551 A | 1/1999 | Woerly | |
| 5,865,846 A | 2/1999 | Bryan et al. | |
| 5,919,235 A | 7/1999 | Husson et al. | |
| 5,922,024 A | 7/1999 | Janzen et al. | |
| 5,976,186 A * | 11/1999 | Bao et al. | 623/17.16 |
| 6,001,130 A | 12/1999 | Bryan et al. | |
| 6,022,376 A | 2/2000 | Assell et al. | |
| 6,093,205 A | 7/2000 | McLeod et al. | |
| 6,099,565 A | 8/2000 | Sakura, Jr. | |
| 6,110,210 A | 8/2000 | Norton et al. | |
| 6,113,639 A | 9/2000 | Ray et al. | |
| 6,132,465 A | 10/2000 | Ray et al. | |
| 6,165,218 A * | 12/2000 | Husson et al. | 623/17.11 |
| 6,187,048 B1 | 2/2001 | Milner et al. | |
| 6,402,784 B1 * | 6/2002 | Wardlaw | 623/17.11 |
| 6,443,988 B2 * | 9/2002 | Felt et al. | 623/17.12 |
| 6,478,796 B2 * | 11/2002 | Zucherman et al. | 606/61 |
| 6,478,800 B1 * | 11/2002 | Fraser et al. | 606/99 |
| 6,488,710 B2 * | 12/2002 | Besselink | 623/17.15 |
| 6,764,514 B1 * | 7/2004 | Li et al. | 623/17.12 |
| 6,805,695 B2 * | 10/2004 | Keith et al. | 606/61 |
| 2002/0173851 A1 * | 11/2002 | McKay | 623/17.11 |
| 2005/0071012 A1 * | 3/2005 | Serhan et al. | 623/17.16 |
| 2005/0131540 A1 * | 6/2005 | Trieu | 623/17.11 |
| 2005/0131541 A1 * | 6/2005 | Trieu | 623/17.11 |
| 2005/0177173 A1 * | 8/2005 | Aebi et al. | 606/105 |
| 2005/0216085 A1 * | 9/2005 | Michelson | 623/17.11 |

FOREIGN PATENT DOCUMENTS

| | | |
|---|---|---|
| WO | WO 90/11740 | 10/1990 |
| WO | WO 95/31946 | 11/1995 |
| WO | WO 9 6/01598 | 1/1996 |
| WO | WO 97/26847 | 7/1997 |
| WO | WO 00/13619 | 3/2000 |
| WO | WO 00/13620 | 3/2000 |
| WO | WO 0234169 | 2/2002 |
| WO | WO 0217824 | 7/2002 |
| WO | WO 03028587 | 10/2003 |
| WO | WO 03047472 | 12/2003 |

* cited by examiner

METHOD AND APPARATUS FOR DELIVERING AN INTERVERTEBRAL DISC IMPLANT

CROSS-REFERENCE TO RELATED APPLICATIONS

This application is a continuation-in-part of U.S. patent application Ser. No. 09/943,441, filed Aug. 30, 2001 now abandoned, and of U.S. patent application Ser. No. 10/459,630, filed Jun. 11, 2003 now abandoned, both of which are continuations-in-part of U.S. patent application Ser. No. 09/650,525, filed Aug. 30, 2000 now U.S. Pat. No. 6,620,196. All of the foregoing are hereby incorporated by reference into this application in their entirety.

FIELD OF THE INVENTION

The present invention relates generally to methods and instruments for delivering a spinal implant, and more particularly to methods and instruments for implanting material to augment, repair, or replace an intervertebral disc nucleus.

BACKGROUND OF THE INVENTION

The intervertebral disc functions to stabilize the spine and to distribute forces between vertebral bodies. A normal disc includes a gelatinous nucleus pulposus, an annulus fibrosis and two vertebral end plates. The nucleus pulposus is surrounded and confined by the annulus fibrosis.

It is known that intervertebral discs are prone to injury and degeneration. For example, herniated discs are common, and typically occur when normal wear, or exceptional strain, causes a disc to rupture. Degenerative disc disease typically results from the normal aging process, in which the tissue gradually looses its natural water and elasticity, causing the degenerated disc to shrink and possibly rupture.

Intervertebral disc injuries and degeneration are frequently treated by replacing or augmenting the existing disc material. Current intervertebral disc replacement procedures tend to utilize full-sized implants, particularly hydrogels, to augment or replace the original disc nucleus. These materials are commonly implanted after first making a hole with a guide wire, and then subsequently enlarging the hole with a succession of sleeves having increased diameters. Alternatively, a larger hole may be made by surgical incision, using a scalpel or a small diameter coring blade.

One problem associated with such implants is that they require a relatively large hole to be cut in the disc annulus to allow introduction of the implant. Since the hole must be large enough to accommodate a full sized implant, the annulus must be plugged or sewn closed after implantation to avoid allowing the implant to be expelled from the disc. This complicates the procedure, adding surgical time and cost, and leaving a less sound annulus when the procedure is complete.

Moreover, the devices heretofore used to deliver a spinal disc implant have been difficult load and operate.

A need therefore exists for a method of implanting a spinal disc implant that avoids the need to make large incisions in the disc annulus. A need also exists for a delivery device that is easy to load, and that minimizes the need to make a large incision. The present invention addresses those needs.

SUMMARY OF THE INVENTION

Briefly describing one aspect of the present invention, there is provided a method of implanting a prosthetic spinal disc nucleus in an intervertebral disc nucleus space. In one embodiment the method comprises:
(a) providing a disc nucleus implant instrument having:
  (i) a lumen or passageway effective for passing a material for augmenting, repairing, or replacing an intervertebral disc nucleus, said passageway having a proximal end and a distal end; and
  (ii) a dilator at the distal end of said lumen or passageway, said dilator being effective for dilating an opening in a disc annulus;
(b) providing an implantable material in the lumen or passageway of said disc nucleus implant instrument, said implantable material being suitable for augmenting, repairing, or replacing an intervertebral disc nucleus, and said implantable material having a first cross-sectional size;
(c) providing a hole in the annulus of an intervertebral disc, said hole having an undilated size that is smaller than the first cross-sectional size of the implantable material, and said hole having a dilated size that is larger than the first cross-sectional size of the implantable material;
(d) introducing the dilator of said disc nucleus implant instrument into the hole in the disc annulus while said hole is not fully dilated;
(e) causing said dilator to dilate, and thus to dilate the hole in the disc annulus;
(f) passing the implantable material through said dilator and into said disc nucleus space while the hole in said disc annulus is dilated; and
(g) withdrawing said disc nucleus implant instrument and allowing said hole in said disc annulus to return to a size smaller than its dilated size.

The method preferably is implemented using a prosthetic disc nucleus having two configurations—a larger configuration and a smaller configuration. In that embodiment the inventive method preferably includes the steps of:
(a) providing a disc nucleus implant instrument having:
  (i) a lumen or passageway for passing a prosthetic disc nucleus, said lumen or passageway having a proximal end and a distal end; and
  (ii) a dilator at the distal end of said lumen or passageway, said dilator being effective for dilating an opening in a disc annulus;
(b) providing a prosthetic disc nucleus having a first configuration and a second configuration, wherein said first configuration presents a first cross-sectional size and said second configuration presents a second cross-sectional size, wherein said first cross-sectional size is larger than said second cross-sectional size;
(c) providing a hole in the annulus of a disc receiving the prosthetic disc nucleus, said hole having an undilated size that is smaller than the first cross-sectional size of said prosthetic disc nucleus, and said hole having a dilated size that is larger than the second cross-sectional size of said prosthetic disc nucleus;
(d) providing said prosthetic disc nucleus in its second configuration in the lumen or passageway of said disc nucleus implant instrument;
(e) introducing the dilator of said disc nucleus implant instrument into the hole in the disc annulus while said hole is not fully dilated;

(f) causing said dilator to dilate, and thus to more fully dilate the hole in the disc annulus;

(g) passing said prosthetic disc nucleus through said dilator and into said disc nucleus space while the disc annulus is more fully dilated and the prosthetic disc nucleus is in its second configuration;

(h) withdrawing said disc nucleus implant instrument and allowing said disc annulus to return to a size smaller than its dilated size; and (i) causing or allowing said prosthetic disc nucleus to assume its first configuration.

In both of the above embodiments the inventive method may use a disc nucleus implant instrument that has an activator for causing the dilator to dilate. The activator may use a lever, an inclined plane, a screw mechanism, or some other means to dilate the dilator.

In another aspect of the present invention there is provided an instrument for implanting a prosthetic spinal disc nucleus, and particularly for implanting a disc nucleus having two configurations as mentioned above. The preferred instrument comprises a pair of channel members pivotally joined at one end, with each channel member having a post located near its joined end and extending radially inward from a sidewall of the channel. The device assumes a loading configuration when the first channel member and the second channel member are pivotally connected at an angle of less than 180 degrees (preferably less than 90 degrees), with the distance between the two posts in the loading configuration corresponding to the distance between two central apertures of a prosthetic disc nucleus when the prosthetic disc nucleus is in a relaxed configuration. The device assumes an implanting configuration when the first channel member and the second channel member are pivoted to an angle of approximately 180 degrees, with the distance between the two posts in the implanting configuration being greater than the distance between the two posts in the loading configuration, and further being sufficiently great to straighten the prosthetic disc nucleus from its relaxed and folded configuration to its implantable and straightened configuration.

The inventive instrument may also include a dilator at the distal end of one channel member, as described above. The dilator may be activated by an activator, which may use a lever, an inclined plane, a screw mechanism; or some other means to dilate the dilator, as previously noted. The instrument assumes a delivering configuration when the first channel member and the second channel member are pivoted to an angle of approximately 180 degrees and the dilator has been activated to dilate a hole in a disc annulus.

Additional embodiments as well as features and advantages of the invention will be apparent to those skilled in the art from the descriptions herein.

DESCRIPTION OF THE PREFERRED EMBODIMENTS

Figure 1:
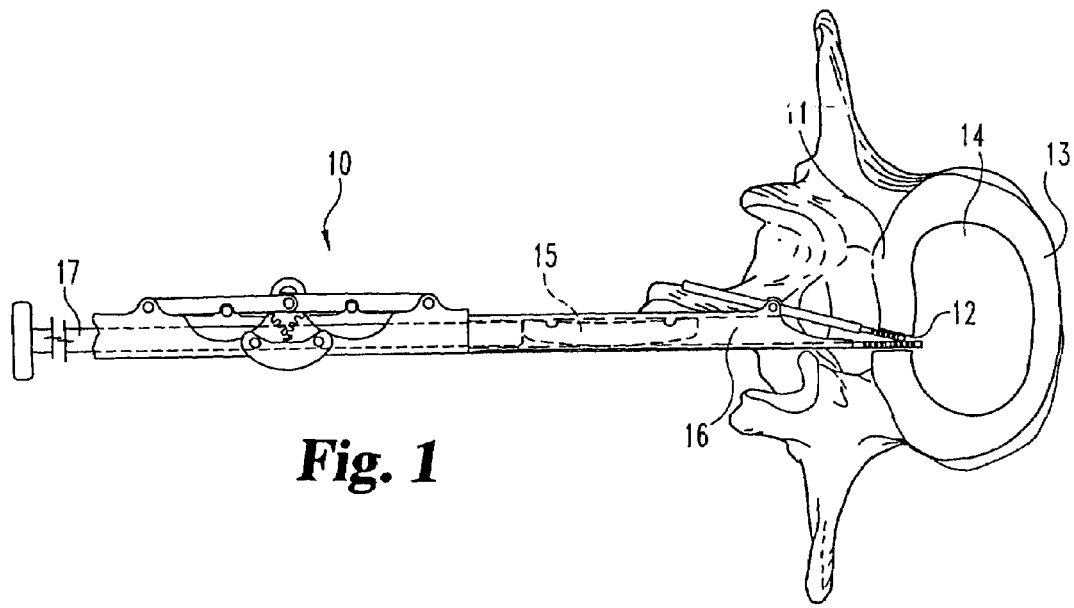
FIG. 1 shows one aspect of the present invention, wherein the disc delivery instrument containing a straightened disc nucleus material has been inserted into a disc annulus and is ready to dilate the annulus hole.

For the purpose of promoting an understanding of the principles of the invention, reference will now be made to preferred embodiments and specific language will be used to describe the same. It will nevertheless be understood that no limitation of the scope of the invention is thereby intended, such alterations and further modifications of the disclosed methods and/or devices, and such further applications of the principles of the invention as described herein, being contemplated as would normally occur to one skilled in the art to which the invention relates.

As indicated above, the present invention provides an improved method and device for implanting a prosthetic intervertebral disc nucleus. In one embodiment the method comprises:

(a) providing a disc nucleus implant instrument having:
  (i) a lumen or passageway effective for passing a material for augmenting, repairing, or replacing an intervertebral disc nucleus, said passageway having a proximal end and a distal end; and
  (ii) a dilator at the distal end of said lumen or passageway, said dilator being effective for dilating an opening in a disc annulus;
(b) providing a disc nucleus material in the lumen or passageway of said disc nucleus implant instrument, said disc nucleus material being suitable for augmenting, repairing, or replacing an intervertebral disc nucleus, and said disc nucleus material having a first cross-sectional size;
(c) providing a hole in the annulus of an intervertebral disc, said hole having an undilated size that is smaller than the first cross-sectional size of the disc nucleus material, and said hole having a dilated size that is larger than the first cross-sectional size of the disc nucleus material;
(d) introducing the dilator of said disc nucleus implant instrument into the hole in the disc annulus while said hole is not fully dilated;
(e) causing said dilator to dilate, and thus to dilate the hole in the disc annulus;
(f) passing the disc nucleus material through said dilator and into said disc nucleus space while the hole in said disc annulus is dilated; and
(g) withdrawing said disc nucleus implant instrument and allowing said hole in said disc annulus to return to a size smaller than its dilated size.

It is to be appreciated from the above description that the inventive method finds utility with any material effective for augmenting, repairing, or replacing an intervertebral disc nucleus. Some materials effective for that purpose are described in greater detail in U.S. patent application Ser. No. 10/245,955, in U.S. patent application Ser. No. 10/645,006, in U.S. patent application Ser. No. 60/426,613, and in U.S. patent application Ser. No. 60/411,514, all of which are incorporated herein by reference in their entirety. Other materials are known to persons skilled in the art, or can be identified without undue experimentation.

The materials implanted by the inventive methods are referred to herein as "disc nucleus material" since they will typically be used as such, even though the material may not come from a disc nucleus. Accordingly, as used herein, a disc nucleus material is any material that is to be used to augment, repair, or replace all or a portion of an intervertebral disc nucleus in the context of this application, regardless of the source of that material.

When a material effective for augmenting, repairing, or replacing an intervertebral disc nucleus has been identified, it is implanted in the disc nucleus space of the disc being repaired. An instrument designed for that purpose, referred to herein as a disc nucleus implant instrument, is preferably used.

As indicated above, the disc nucleus implant instrument includes a lumen or passageway effective for passing the disc nucleus material into an intervertebral disc nucleus. The lumen or passageway has a proximal end and a distal end. The lumen or passageway is sized and configured to allow passage of the disc nucleus material from the proximal end of the passageway to the distal end of the passageway, and is accordingly preferably straight and smooth on its interior surface. Ridges, indentations, projections, etc., may be provided on the interior surface to the extent they assist in, or do not prevent, passage of the material through the lumen or passageway.

Preferred instruments include a lumen or passageway having an inner diameter of between about 2 mm to about 20 mm, with an inner diameter of between about 5 mm and about 10 mm being more preferred. The length of the lumen or passageway is preferably between about 5 cm and about 30 cm, with a length of between about 10 cm and about 25 cm being more preferred.

The disc nucleus implant instrument also preferably includes a dilator at the distal end of the lumen or passageway. The dilator is designed to be effective for dilating a small opening in a disc annulus so that the opening is made large enough for the material being implanted to pass through. The dilator should dilate the opening without tearing the annulus, so that the dilated opening shrinks back to a smaller size after the disc nucleus implant instrument is removed.

One preferred dilator comprises a multiplicity of arms that may be spread apart to dilate a hole in an annulus. The arms preferably end in small tips that may be inserted into relatively small openings in the annulus. The arms are designed to facilitate dilating a small hole so that the hole can temporarily be made large enough to allow passage of the disc nucleus material. Several preferred embodiments of the dilator portion of the instrument are described in greater detail below.

To implant the material a small incision (preferably a hole) is first cut in the annulus of the disc being repaired or augmented. A guide wire or other small instrument may be used to make the initial hole. If necessary, successively larger holes are cut from an initially small puncture. The purpose of the hole (also called an aperture, an opening, or a portal, for example) is to allow passage of the new disc nucleus material, so that the material can be implanted into the disc nucleus space from the side (i.e, through the annulus). It is important, though, for the hole to be as small as possible to minimize expulsion of the material through the hole after the surgery is complete.

Once a small hole is provided, the tip of the disc nucleus implant instrument is inserted into the hole. The dilator is then used to dilate the hole, making it large enough to deliver the material being used to replace or augment the disc nucleus. The dilator preferably stretches the hole temporarily, and avoids tearing so that the hole can return back to its undilated size after the instrument is removed. Even if some tearing or permanent stretching occurs, the dilation is preferably accomplished in a manner that allows the hole to return to a size smaller than its dilated size after the surgery is complete.

The material being used to replace or augment the disc nucleus is then implanted into the disc nucleus space, typically by pushing it through the lumen or passageway of the instrument, through the dilated hole in the annulus, and finally into the disc nucleus space. The tip of the instrument may be moved from side-to-side, or from front-to-back, as necessary to deliver the material uniformly throughout the disc nucleus space.

After the material is delivered into the disc nucleus space, the instrument is withdrawn and the hole in the annulus is allowed to return to its original size. If the annulus has been stretched or torn so that it does not return to its original size, it should at least return to a size smaller than its dilated size.

In one preferred embodiment the method described above is used to deliver a material that has two configurations—a first configuration and a second configuration—wherein one of the configurations presents a cross section that is smaller than the other configuration. With this embodiment it is possible to implant the material through the dilated annular opening when the material is in its smaller configuration, and then cause or allow the material to assume its larger configuration after it has been passed through the dilated hole in the annulus. Briefly summarizing this aspect of the invention, one preferred embodiment comprises:

(a) providing a disc nucleus implant instrument having:
(i) a lumen or passageway for passing a prosthetic disc nucleus, said lumen or passageway having a proximal end and a distal end; and
(ii) a dilator at the distal end of said lumen or passageway, said dilator being effective for dilating an opening in a disc annulus;

(b) providing a prosthetic disc nucleus having a first configuration and a second configuration, wherein said first configuration presents a first cross-sectional size and said second configuration presents a second cross-sectional size, wherein said first cross-sectional size is larger than said second cross-sectional size;

(c) providing a hole in the annulus of a disc receiving the prosthetic disc nucleus, said hole having an undilated size that is smaller than the first cross-sectional size of said prosthetic disc nucleus, and said hole having a dilated size that is larger than the second cross-sectional size of said prosthetic disc nucleus;

(d) providing said prosthetic disc nucleus in its second configuration in the passageway of said disc nucleus implant instrument;

(e) introducing the dilator of said disc nucleus implant instrument into the hole in the disc annulus while said hole is not fully dilated;

(f) causing the dilator to dilate, and thus to more fully dilate the hole in the disc annulus; and (g) passing said prosthetic disc nucleus through said dilator and into said disc nucleus space while the disc annulus is more fully dilated and the prosthetic disc nucleus is in its second configuration;

(h) withdrawing said disc nucleus implant instrument and allowing said disc annulus to return to a size smaller that its dilated size; and (i) causing or allowing said prosthetic disc nucleus to assume its first configuration.

It is to be appreciated that the inventive method described above finds particular utility with materials described in U.S. patent application Ser. No. 10/645,006, and in U.S. patent application Ser. No. 60/426,613. Both of those applications disclose materials that may be dehydrated prior to implantation, and are then rehydrated to a larger size after implantation. The inventive method described above also finds particular utility with materials described in U.S. patent application Ser. No. 09/943,441, which discloses implants having a shape memory that allows the implant to be straightened to a straightened configuration having a smaller cross section before implantation, and then relaxed to a folded configuration having a larger cross section after implantation.

Figure 35:
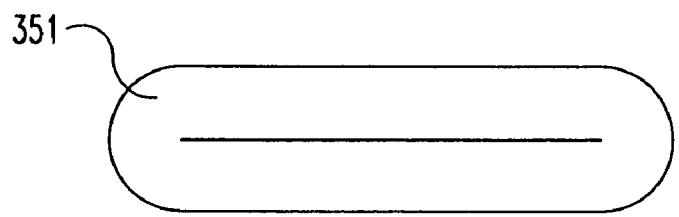
FIG. 35 shows a plug of disc annulus material used to make an implant according to one embodiment of the present invention.
Figure 36:
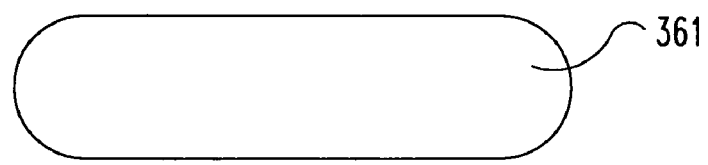
FIG. 36 shows a straightened segment of disc annulus material used to make an implant according to one embodiment of the present invention.
Figure 37:
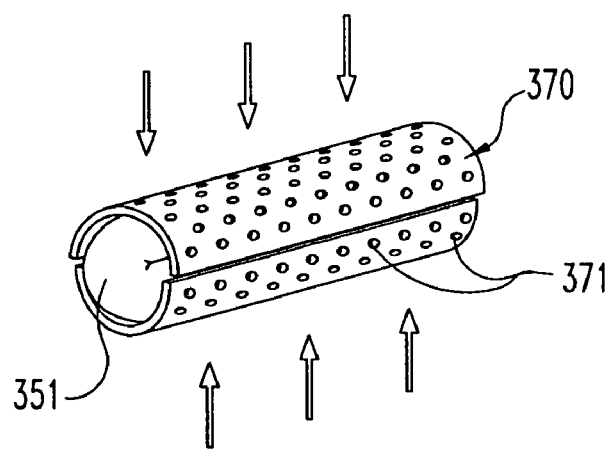
FIG. 37 shows disc annulus material being compressed to make an implant according to one embodiment of the present invention.
Figure 38:
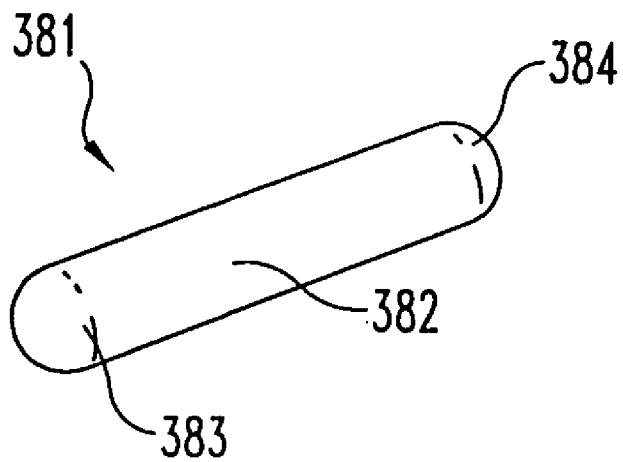
FIG. 38 shows compressed disc annulus material effective for use as an implant according to one embodiment of the present invention.
Figure 39:
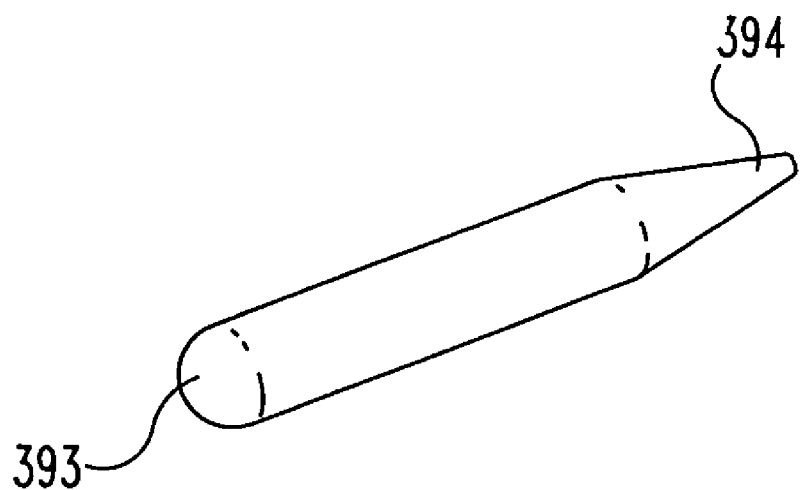
FIG. 39 shows an alternative embodiment of compressed disc annulus material effective for use as an implant according to one embodiment of the present invention.

For example, FIGS. 35–39 show one preferred embodiment of making an implant according to the present invention. In that embodiment, a plug of disc annulus material is formed from either a compressed whole disc annulus 351 as shown in FIG. 35, or a straightened segment of disc annulus 361 as shown in FIG. 36. A mold 370 of a porous material, such as a surgical steel mesh, having openings 371 large enough for fluid to pass through, is placed around the disc annulus material, and is used to compress the material radially inward, as shown in FIG. 37. By pushing the mold inward around disc annulus material, the material can be compressed to a more compact size, as shown by implant 381 in FIG. 38. The illustrated compressed implant 381 comprises an implant having a middle portion 382, and two end portions 383 and 384.

In the preferred embodiment, compressed implant 381 is dehydrated so that it retains its compact shape. After dehydration, implant 381 may be further shaped, such as by providing either or both of end 383 and 384 with a reduced diameter, such as a rounded end 393 or a point 394.

Alternatively, FIGS. 16–18 (discussed in more detail below) show an alternative embodiment of an implant that may be used in the present invention. Referring to these figures, implant 160 comprises a folded implant having shape memory so that it can be unfolded for implantation, yet returns to its folded configuration when relaxed in the disc nucleus space. As described in U.S. patent application Ser. No. 09/943,441, implant 160 has two arms 161 and 162 that are folded over to create inner fold 163. The arms preferably abut one another at their ends when in the folded configuration, and also abut the middle portion of the implant. This creates an implant having a substantially solid center core, and provides the support necessary to avoid compression of the disc nucleus in most patients.

Additionally, the illustrated implants may have external side surfaces that include at least one groove extending along the surface to advantageously further relieve the compressive force on the external side of the implant when the implant is deformed into a substantially straightened, or otherwise unfolded configuration. This allows extensive short-term deformation without permanent deformation, cracks, tears or other breakage. For example, implant 160 shown in FIGS. 16–18, includes a plurality of grooves 167 disposed along its external surface, with the grooves typically extending from the top surface to the bottom surface of the implant. When dividing the implant in half, thus more easily viewing a first side $S_1$ and a second side $S_2$, with a plane passing through the width of the implant along axis X, it can be seen in FIG. 16 that four grooves are present on first side $S_1$ and four grooves are present on second side $S_2$, although more or less may be present depending on the case. It is preferred that at least one groove is present on each side $S_1$ and $S_2$.

As to the specifics of the method used to deliver the "two configuration" implants, the basic principles of cutting a small hole in the disc annulus and dilating the annulus enough to allow the disc nucleus material to pass through the hole still apply. In this embodiment though, when the instrument is withdrawn the material is caused or allowed to assume a shape and/or size larger than the shape/size that was presented when the material was implanted. For example, when a dehydrated material is used, the material is allowed to swell up in the disc space so that the rehydrated material is larger than the dehydrated material. Then, when the instrument is withdrawn and the hole in the annulus returns to a smaller size, the disc nucleus material finds it even more difficult to fit back through the hole. This further mitigates the need for an annular plug or sutures to prevent expulsion of the disc nucleus material.

When shape memory implants such as those disclosed in U.S. patent application Ser. No. 09/943,441 are being used, the method may include the step of unfolding the implant so that it assumes a "straightened" configuration in the delivery instrument. The implant may then be delivered through the dilated hole while in that straightened configuration. After implantation, the implant returns naturally to its relaxed, folded configuration that mimics the shape of a natural disc. In this folded configuration the implant is too large to easily fit back through the undilated hole.

Describing now one disc nucleus implant instrument that may be used in the present invention, and particularly an instrument to deliver one preferred embodiment of a "two configuration" disc nucleus material, in one embodiment the device preferably comprises:

(a) a channel member having a first end and a second end;

(b) means for converting a disc nucleus implant from a first, folded configuration to a second, straightened configuration;

(c) means for positioning said disc nucleus implant in said channel member while said disc nucleus implant is in its second straightened configuration; and (d) means for moving said disc nucleus implant through said channel and into an intervertebral disc space while the implant remains substantially in its straightened configuration.

More specifically describing the most preferred embodiments of a disc nucleus implant instrument that may be used in the present invention, and particularly an instrument to deliver one preferred embodiment of a "two configuration" disc nucleus material, in one embodiment the device preferably comprises:

(a) a first channel member having a first end and a second end, said first channel member defining a channel from said first end to said second end, said channel comprising at least one side wall;

(b) a post extending radially inward from said first channel member side wall, said post being located near the first end of said first channel member;

(c) a second channel member having a first end and a second end, said second channel member defining a channel from said first end to said second end, said channel comprising at least one side wall;

(d) a post extending radially inward from said second channel member side wall, said post being located near the first end of said second channel member;

wherein said first channel member and said second channel member are pivotally connected at their respective first ends;

wherein the device assumes a loading configuration when the first channel member and the second channel member are pivotally connected to define an angle of less than 180 degrees; and wherein the device assumes an implanting configuration when the first channel member and the second channel member are pivotally connected to define an angle of approximately 180 degrees.

In other embodiments the device may include a locking mechanism to lock the device in its implanting configuration. As will be described further below, the locking mechanism locks the instrument in a manner that maintains the angle of approximately 180 degrees, keeping the implant in its straightened configuration and thus facilitating implantation.

Additionally, a dilator may be included at the distal end of one channel member, with an activator being optionally included to dilate the dilator. Preferred activators use a lever, an inclined plane, or a screw mechanism to cause the dilator to dilate.

In any of the disclosed embodiments, and as briefly described above, the spinal disc implant delivery device may include a first arm and a second arm extending from opposing sides of one channel member. The arms comprise one preferred embodiment of the dilator portion of the instrument, and are used to enter and dilate the hole in the annulus. The first arm and second arm may be rigid, or either of them may be flexible. Preferably, one arm is rigid (i.e., immovable) and the other arm is flexible. Also contemplated are devices having a first arm and a second arm where both arms are either rigid or flexible.

Further, at least one arm may comprise a tip having teeth. By having "teeth" it is meant that the tip is designed to include teeth-like extensions around the edges of the tip. This design allows for an arm to move more easily through bony structures commonly encountered when performing spinal surgeries.

When an instrument having a dilator is used to implant a shape memory implant as described above, one aspect of the present invention provides a method comprising:

(a) providing a disc nucleus implant instrument having:
(i) a first channel member having a first end and a second end, said first channel member defining a channel from said first end to said second end, said channel comprising at least one side wall;
(ii) a first post extending radially inward from said first channel member side wall, said post being located near the first end of said first channel member;
(iii) a second channel member having a first end and a second end, said second channel member defining a channel from said first end to said second end, said channel comprising at least one side wall; and
(iv) a second post extending radially inward from said second channel member side wall, said post being located near the first end of said second channel member;

wherein said first channel member and said second channel member are pivotally connected at their respective first ends;

wherein the device assumes a loading configuration when the first channel member and the second channel member are pivotally connected to define an angle of less than 180 degrees; and wherein the device assumes an implanting configuration when the first channel member and the second channel member are pivotally connected to define an angle of approximately 180 degrees;

(b) providing a prosthetic disc nucleus comprising a load bearing elastic body having shape memory and sized for placement into an intervertebral disc space, said body having a first end, a second end, and a central portion; wherein said shape memory biases said body to a first configuration wherein said first end and said second end are positioned adjacent to said central portion to form at least one inner fold and to provide a substantially solid center core when the implant is in its first configuration; said elastic body configurable into a second, straightened configuration for insertion through an opening in an intervertebral disc annulus fibrosis; wherein said shape memory returns said body to said first configuration after said insertion; wherein said prosthetic disc nucleus presents a first cross-sectional size when in its first configuration, and a second cross-sectional size when in its second configuration, wherein said first cross-sectional size is larger than said second cross-sectional size;

(c) loading said prosthetic disc nucleus into said disc nucleus implant instrument such that said post extending radially inward from said first channel member side wall and said post extending radially inward from said second channel member side wall each are positioned in the inner fold of the prosthetic disc nucleus;

(d) converting said disc nucleus implant instrument from its loading configuration to its implanting configuration, thereby moving said first post and said second post farther apart from each other and straightening the prosthetic disc nucleus from its first configuration to its second configuration;

(e) providing a hole in the annulus of a disc receiving the prosthetic disc nucleus, said hole having an undilated size that is smaller than the first cross-sectional size of said prosthetic disc nucleus, and said hole having a dilated size that is larger than the second cross-sectional size of said prosthetic disc nucleus;

(f) introducing the dilator of said disc nucleus implant instrument into the hole in the disc annulus while said hole is not fully dilated;

(g) causing the dilator to dilate, and thus to more fully dilate the hole in the disc annulus; and (h) passing said prosthetic disc nucleus through said dilator and into said disc nucleus space while the disc annulus is more fully dilated and the prosthetic disc nucleus is in its second configuration;

(i) withdrawing said disc nucleus implant instrument and allowing said disc annulus to return to a size smaller that its dilated size; and (j) causing or allowing said prosthetic disc nucleus to assume its first configuration.

As to other disc nucleus implants that may be used in the present invention, some spinal disc implants comprise a biomechanical or otherwise flexible material to facilitate its conversion from a loading configuration to a deliverable configuration. Further, the spinal disc implant may include a load bearing elastic body surrounded by an outer, preferably resorbable or otherwise temporary, shell. The outer shell advantageously anchors the elastic body within the intervertebral disc space. The surface of the implant may include various surface features, including various macro-surface patterns, and chemical or physical modifications to further enhance fixation of the implant. The surface features, such as the macro-surface patterns and physical modifications, for example, may enhance fixation of the elastic body to the outer shell, or they may enhance fixation to surrounding tissue such that, in certain forms of the invention, no outer shell is needed.

The dimensions of the spinal disc implants used herein may vary depending on the particular case, but the implant is typically sized for introduction into an intervertebral disc nucleus space. Moreover, the implant is preferably wide enough to support adjacent vertebrae and is of a height sufficient to separate the adjacent vertebrae.

The spinal disc implants used in the invention may be fabricated in a wide variety of shapes, as desired for a particular application. Although the implant may assume a variety of shapes, it is typically shaped to conform to the shape of the natural nucleus pulposus, at least when in its hydrated and/or relaxed configuration. Thus, the implants may be substantially elliptical when in their hydrated and/or relaxed configurations. In other forms of the invention, the shape of the implants in their hydrated and/or relaxed configurations may be generally annular-shaped, cylindrical-shaped, or otherwise shaped as required to conform to the intervertebral disc cavity.

The spinal disc implants are also shaped in a manner to allow easy implantation into a spinal disc nucleus space. Accordingly, the implant may have a narrow, tubular shape when in its dehydrated and/or straightened configuration, and may include at least one narrow or pointed end to facilitate implantation through a small annulus hole.

Although the implants may be formed as a one-piece implant, it may also be formed as a multi-piece implant. When one-piece implants are used, they may be used individually or they may be used in a combination of two or more implants. When multi-piece implants are used, the pieces may be used independently or they may be joined together. In some embodiments one-piece implants and multi-piece implants are used together.

A spinal disc implant for use in the invention may be formed from a wide variety of biocompatible polymeric materials, including elastic materials, such as elastomeric materials, hydrogels or other hydrophilic polymers, or composites thereof. Suitable elastomers include silicone, polyurethane, copolymers of silicone and polyurethane, polyolefins, such as polyisobutylene and polyisoprene, neoprene, nitrile, vulcanized rubber and combinations thereof. The vulcanized rubber described herein may be produced, for example, by a vulcanization process utilizing a copolymer produced as described, for example, in U.S. Pat. No. 5,245,098 to Summers et al. from 1-hexene and 5-methyl-1,4-hexadiene. Suitable hydrogels include natural hydrogels, and those formed from polyvinyl alcohol, acrylamides such as polyacrylic acid and poly (acrylonitrile-acrylic acid), polyurethanes, polyethylene glycol, poly (N-vinyl-2-pyrrolidone), acrylates such as poly (2-hydroxy ethyl methacrylate) and copolymers of acrylates with N-vinyl pyrrolidone, N-vinyl lactams, acrylamide, polyurethanes and polyacrylonitrile, or may be other similar materials that form a hydrogel. The hydrogel materials may further be cross-linked to provide further strength to the implant. Examples of polyurethanes include thermoplastic polyurethanes, aliphatic polyurethanes, segmented polyurethanes, hydrophilic polyurethanes, polyether-urethane, polycarbonate-urethane and silicone polyetherurethane. Other suitable hydrophilic polymers include naturally occurring materials such as glucomannan gel, hyaluronic acid, polysaccharides, such as cross-linked carboxyl-containing polysaccharides, and combinations thereof. The nature of the materials employed to form the elastic body should be selected so the formed implants have sufficient load bearing capacity. In preferred embodiments, a compressive strength of at least about 0.1 Mpa is desired, although compressive strengths in the range of about 1 Mpa to about 20 Mpa are more preferred.

When the implants are formed from an elastic material, such as a hydrogel, or other similar hydrophilic material, or include a resorbable outer shell, they may advantageously deliver desired pharmacological agents. The pharmacological agent may be a growth factor that may advantageously repair the endplates and/or the annulus fibrosis. For example, the growth factor may include an osteoinductive factor (e.g., a bone morphogenetic protein), transforming growth factor-ss (TGF-ss), insulin-like growth factor, platelet derived growth factor, fibroblast growth factor or other similar growth factor or combination thereof having the ability to repair the endplates and/or the annulus fibrosis of an intervertebral disc. Preferably, the spinal disc implant comprises an osteoinductive factor.

Osteoinductive factors can be defined as those factors, which stimulate uncommitted cells, e.g., mesenchymal stem cells, to convert phenotypically to chondroprogenitor and osteoprogenitor cells. Osteogenic factors include those factors that contain cells that are committed to osteoblastic phenotypes or stimulate committed osteoprogenitor cells and mature osteoblasts to proliferate. Thus, the major distinction between the two factors is that cellular proliferation characterizes an osteogenic factor, whereas cellular differentiation characterizes an osteoinductive factor. It will be understood that an osteoinductive factor and osteogenic factor can be contained in a spinal disc implant either alone, or in combination, providing for a synergistic effect.

Suitable osteoinductive factors for use in the invention include growth factors to stimulate or induce bone growth, including factors comprised of protein or genes. Recombinant human bone morphogenetic proteins (rhBMPs) are preferred. Most preferably, the bone morphogenetic protein is a rhBNMP-2, rhBMP-4 or heterodimers thereof. Bone morphogenic protein (BMP), an osteoinductive cytokine extracted from bone matrix, is capable of inducing bone formation when implanted in a fracture of surgical bone site. BMP actually refers to a group of bone morphogenic proteins belonging to the TGF-β superfamily. The structures of eleven proteins, BMP-1 through BMP-13 have been elucidated. Recombinantly produced human bone morphogenic protein-2 has been demonstrated in several animal models to be effective in regenerating bone in skeletal defects. BMPs are commercially available from Genetics Institute, Inc., Cambridge, Mass. And may also be prepared by one skilled in the art as described in U.S. Pat. Nos. 5,187,076; 5,366,875; 5,108,922; 5,116,738; 5,013,649; 6,352,972 and International PCT Applications WO93/00432; WO94/26893; WO94/26892.

Recombinant BMP-2 can be used at a concentration of about 0.4 mg/ml to about 4.0 mg/ml, preferably about 1.0 to 3.0 mg/ml. However, any bone morphogenetic protein is contemplated including bone morphogenetic proteins designated as BMP-1 through BMP-13. BMPs are available from Genetics Institute, Inc., Cambridge, Mass. and may also be prepared by one skilled in the art as described in U.S. Pat. No. 5,187,076 to Wozney et al.; U.S. Pat. No. 5,366,875 to Wozney et al.; U.S. Pat. No. 4,877,864 to Wang et al.; U.S. Pat. No. 5,108,922 to Wang et al.; U.S. Pat. No. 5,116,738 to Wang et al.; U.S. Pat. No. 5,013,649 to Wang et al.; U.S. Pat. No. 5,106,748 to Wozney et al.; and PCT Patent Nos. WO93/00432 to Wozney et al.; WO94/26893 to Celeste et al.; and WO94/26892 to Celeste et al. All osteoinductive factors are contemplated whether obtained as above or isolated from bone. Methods for isolating bone morphogenetic protein from bone are described in U.S. Pat. No. 4,294,753 to Urist and Urist et al., 81 PNAS 371,1984.

In other forms of the invention, the spinal disc implants may comprise a pharmacological agent used for treating various spinal conditions, including degenerative disc disease, spinal arthritis, spinal infection, spinal tumor and osteoporosis.

Such agents include antibiotics, analgesics, anti-inflammatory drugs, including steroids, and combinations thereof. Other such agents are well known to the skilled artisan. These agents are also used in therapeutically effective amounts. Such amounts may be determined by the skilled artisan depending on the specific case.

The pharmacological agents are preferably dispersed within the hydrogel, or other hydrophilic, implant for in vivo release, and/or, with respect to the implants with the resorbable outer shell, may be dispersed in the outer shell. The hydrogel can be cross-linked chemically, physically, or by a combination thereof, in order to achieve the appropriate level of porosity to release the pharmacological agents at a desired rate. The agents may be released upon cyclic loading, and, in the case of implants including a resorbable outer shell, upon resorption of the shell.

The pharmacological agents may be dispersed in the implants by adding the agents to the solution used to form the implant, by soaking the formed implant in an appropriate solution containing the agent, or by other appropriate methods known to the skilled artisan. In other forms of the invention, the pharmacological agents may be chemically or otherwise associated with the implant. For example, the agents may be chemically attached to the outer surface of the implant.

Referring now to the drawings, FIG. 1 shows a spinal disc implant delivery device 10 after the dilator 11 has been inserted into a hole 12 in a disc annulus 13. The longest part of the tip of the instrument is positioned in the disc nucleus space 14. Disc nucleus implant 15 is loaded in its unfolded configuration in the passageway 16 of instrument 10. Plunger 17 is positioned to push implant 15 through passageway 16 into disc nucleus space 14 after annulus hole 12 is dilated.

Figure 2:
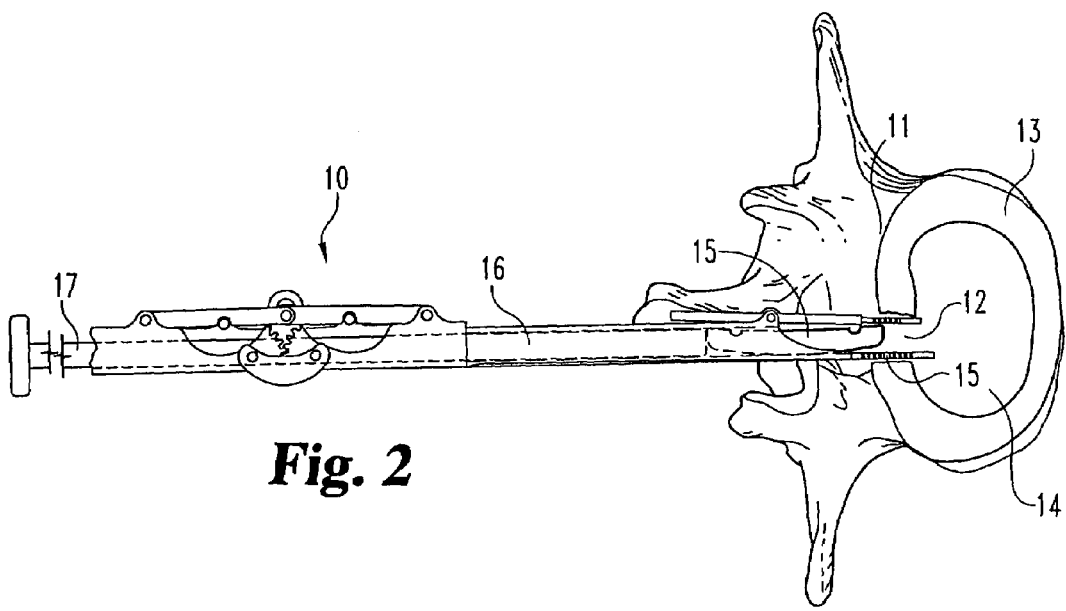
FIG. 2 shows a further aspect of the present invention, wherein the disc delivery instrument has been inserted into a disc annulus and has dilated the annulus hole.

FIG. 2 shows device 10 after dilator 11 has dilated hole 12 in disc annulus 13. The tip of the instrument remains positioned so that it just enters disc nucleus space 14, and disc nucleus implant 15 remains loaded in passageway 16 of instrument 10. Plunger 17 has now begun to push implant 15 through passageway 16 into disc nucleus space 14.

Figure 3:
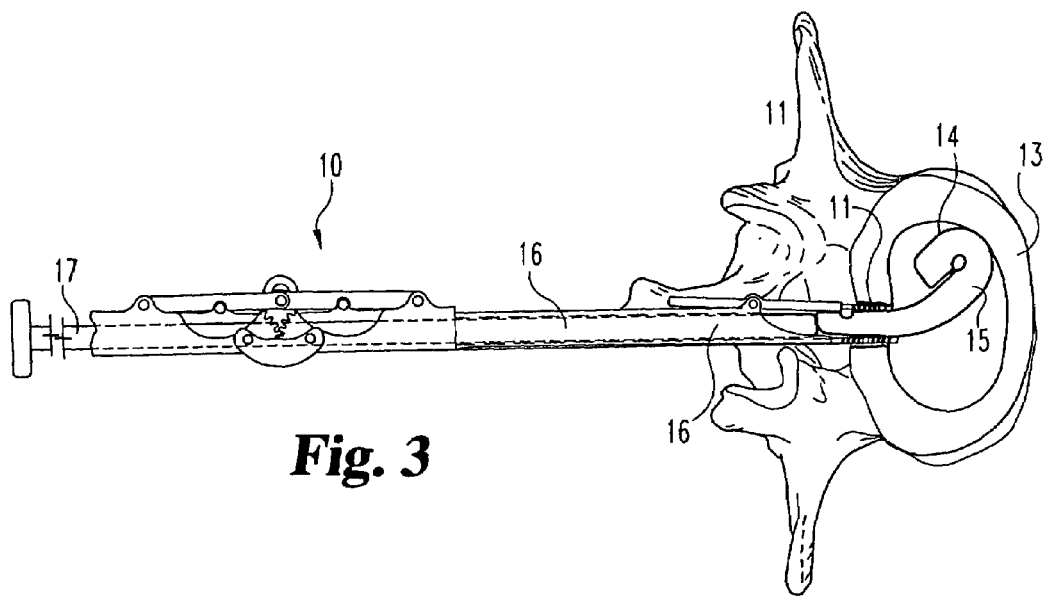
FIG. 3 shows a further aspect of the present invention, wherein a disc nucleus material is being delivered into a disc nucleus space through the dilated annulus hole.

FIG. 3 shows device 10 as disc nucleus implant 15 is being delivered through dilated hole 12 into the disc nucleus space 14. Disc nucleus implant 15 is beginning to fold back to its relaxed, folded configuration as implant 15 leaves passageway 16 and enters disc nucleus space 14.

Figure 4:
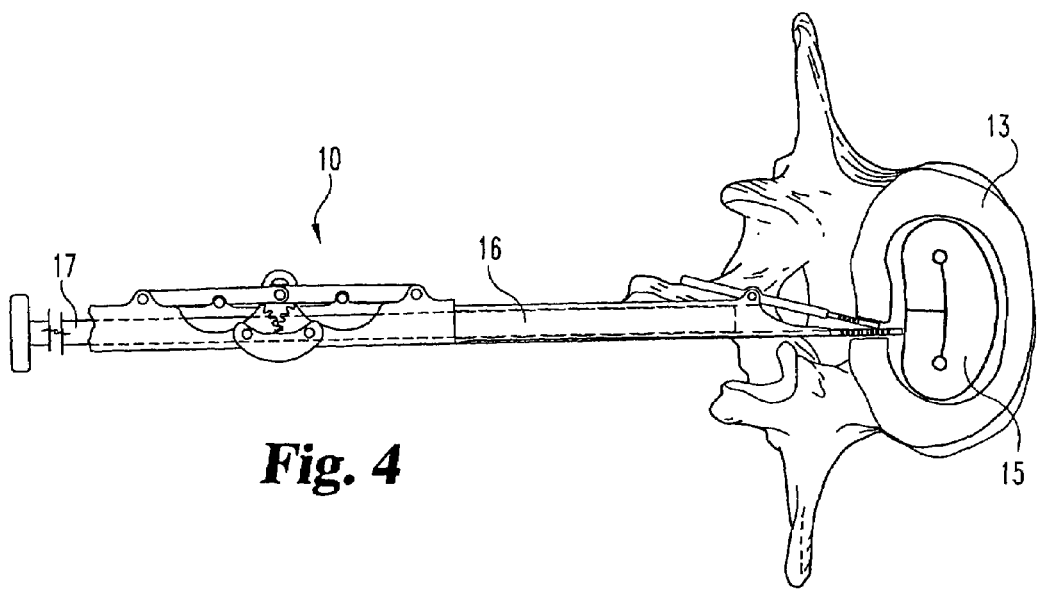
FIG. 4 shows a further aspect of the present invention, wherein a disc nucleus material has been delivered into a disc nucleus space through the dilated annulus hole.

FIG. 4 shows device 10 immediately after disc nucleus implant 15 has been delivered through dilated hole 12 into the disc nucleus space 14. Disc nucleus implant 15 has folded to its relaxed, folded configuration, but hole 12 in annulus 13 remains dilated until the instrument is withdrawn.

Figure 5:
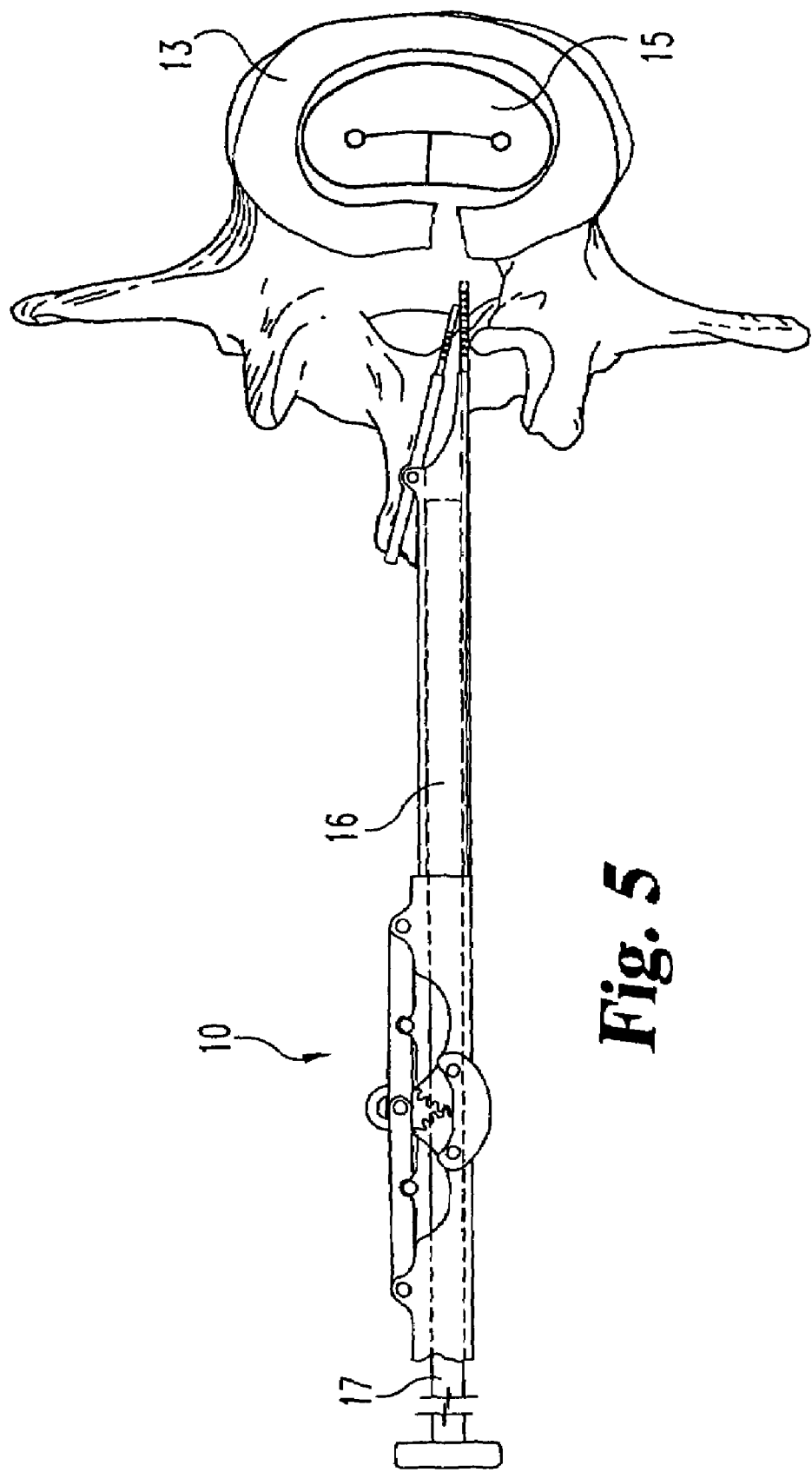
FIG. 5 shows a further aspect of the present invention, wherein the disc delivery instrument has been withdrawn from the disc annulus hole, and the implanted disc nucleus material has assumed its relaxed configuration.

FIG. 5 shows the implanted disc nucleus implant 15 after the instrument has been withdrawn. Hole 12 in annulus 13 has returned to a size smaller than its dilated size. Implant 15, which fit through annulus hole 12 when hole 12 was dilated and implant 15 was unfolded, does not fit back through the undilated hole.

Figure 6:
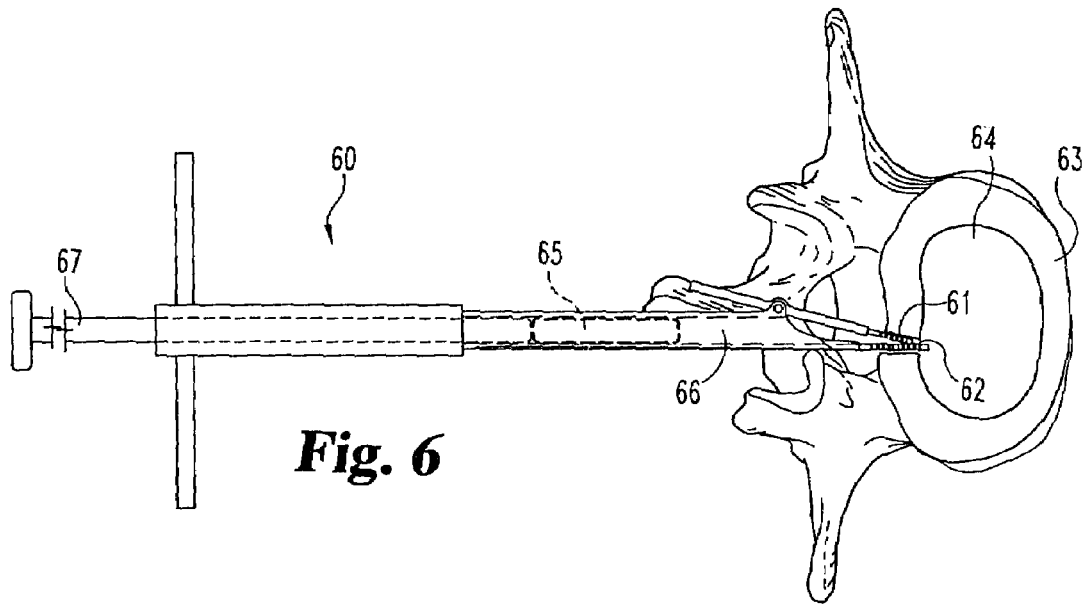
FIG. 6 shows another aspect of the present invention, wherein the disc delivery instrument containing a dehydrated disc nucleus material has been inserted into a disc annulus and is ready to dilate the annulus hole.

FIG. 6 shows another spinal disc implant delivery device 60 after the dilator 61 has been inserted into a hole 62 in disc annulus 63. The tip of the instrument is positioned in the disc nucleus space 64. Disc nucleus implant 65 is loaded in its dehydrated configuration in the passageway 66 of instrument 60. Plunger 67 is positioned to push implant 65 through passageway 66 into disc nucleus space 64 after annulus hole 62 is dilated.

Figure 7:
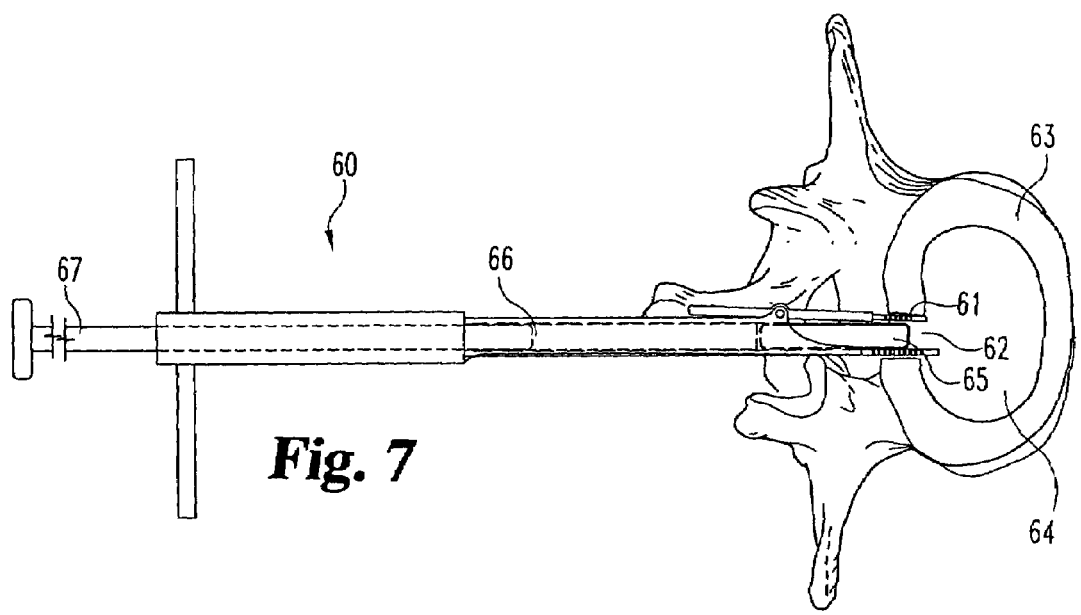
FIG. 7 shows a further aspect of the present invention, wherein the disc delivery instrument has been inserted into a disc annulus and has dilated the annulus hole.

FIG. 7 shows device 60 after dilator 61 has dilated hole 62 in disc annulus 63. The tip of the instrument remains positioned in the disc nucleus space 64, and disc nucleus implant 65 remains loaded in the passageway 66 of instrument 60. Plunger 67 has now begun to push implant 65 through passageway 66 into disc nucleus space 64.

Figure 8:
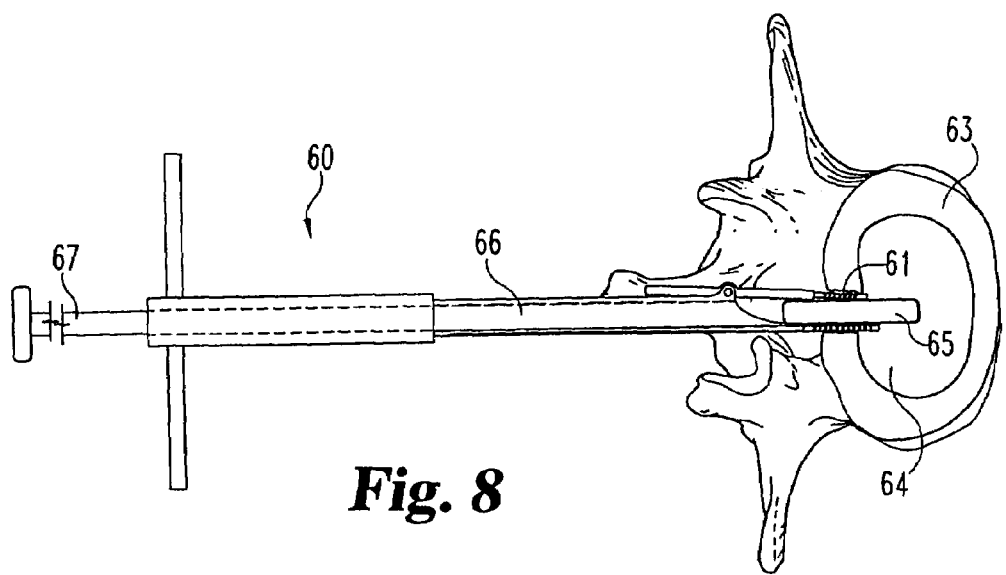
FIG. 8 shows a further aspect of the present invention, wherein a disc nucleus material is being delivered into a disc nucleus space through the dilated annulus hole.

FIG. 8 shows device 60 as disc nucleus implant 65 is being delivered through dilated hole 62 into the disc nucleus space 64. Disc nucleus implant 65 remains dehydrated as it leaves passageway 66 and enters disc nucleus space 64.

Figure 9:
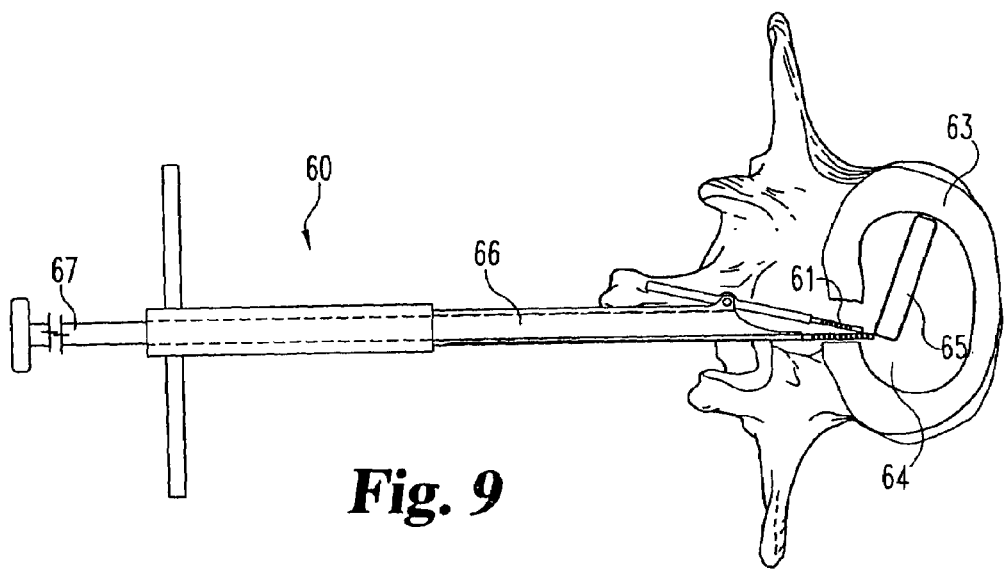
FIG. 9 shows a further aspect of the present invention, wherein a dehydrated disc nucleus material has been delivered into a disc nucleus space through the dilated annulus hole.

FIG. 9 shows device 60 immediately after disc nucleus implant 65 has been delivered through dilated hole 62 into the disc nucleus space 64. Disc nucleus implant 65 has not yet begun to rehydrate, and hole 62 in annulus 63 remains dilated since the instrument has not yet been withdrawn.

Figure 10:
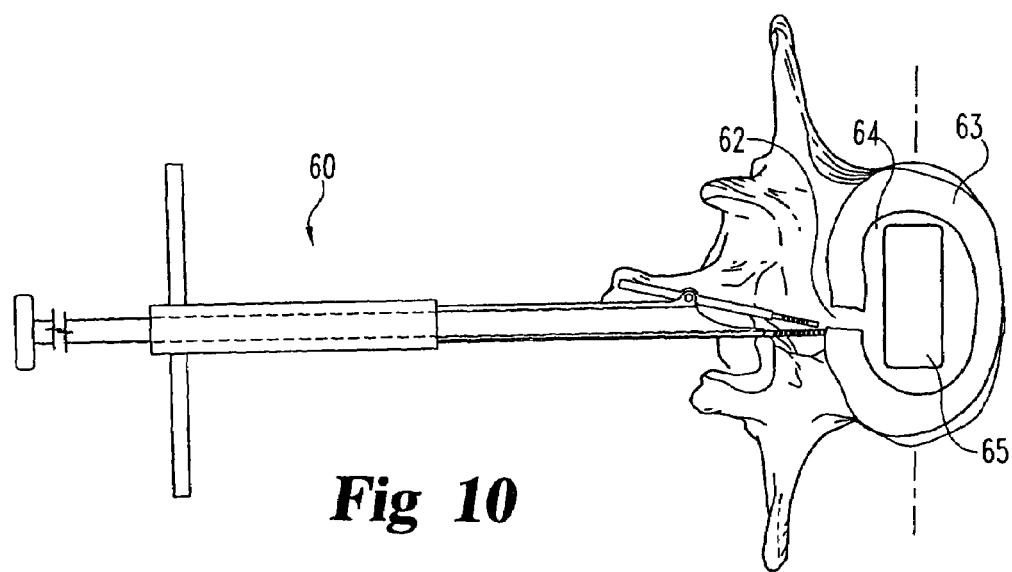
FIG. 10 shows a further aspect of the present invention, wherein the disc delivery instrument has been withdrawn from the disc annulus hole, and the implanted disc nucleus material is beginning to rehydrate.

FIG. 10 shows the implanted disc nucleus implant 65 after the instrument has been withdrawn and the implant has rehydrated. Hole 62 in annulus 63 has returned to a size smaller than its dilated size. Rehydrated disc nucleus implant 65 will no longer fit back though disc annulus hole 62.

Figure 11:
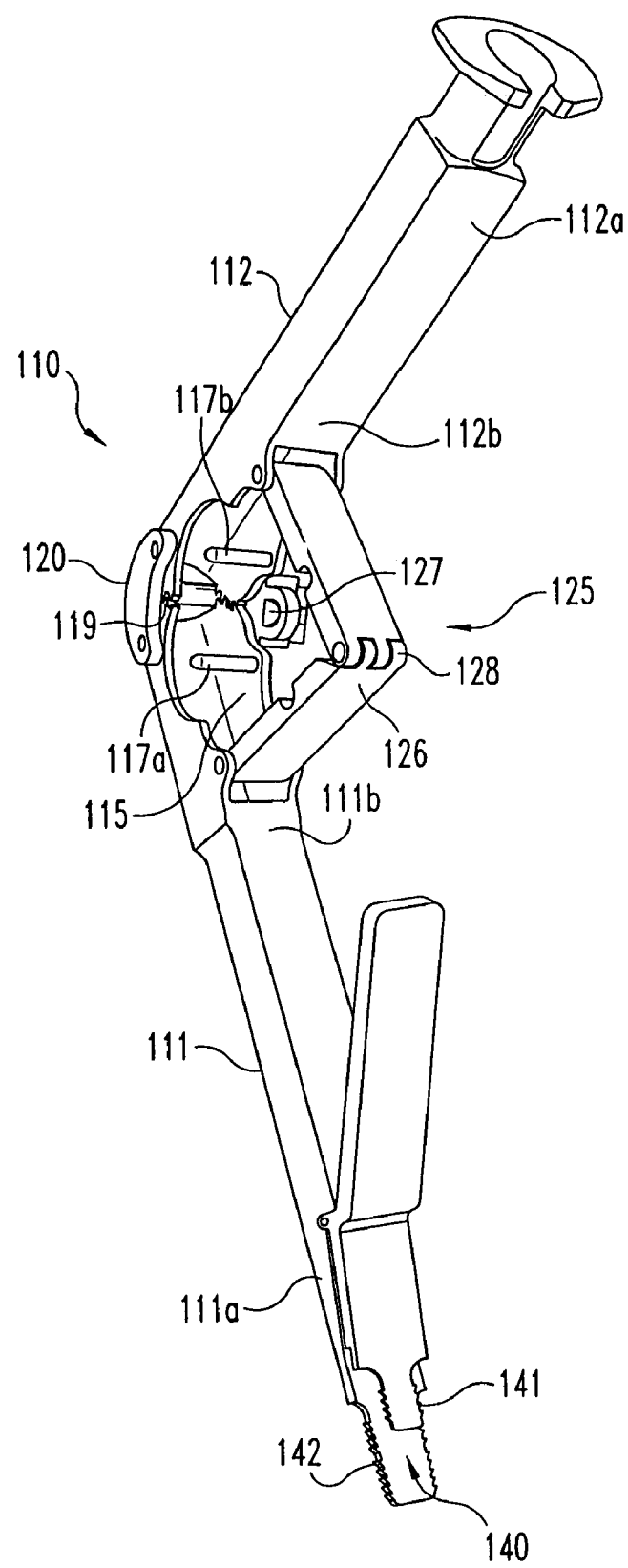
FIG. 11 shows a further aspect of the present invention, wherein the disc delivery instrument has been withdrawn from the disc annulus hole, and the implanted disc nucleus material has assumed its rehydrated configuration.

FIG. 11 shows one embodiment of a preferred disc nucleus delivery device useful for delivering folded nucleus implants of the type illustrated in FIGS. 1–5. Device 110 includes a first channel member 111 and a second channel member 112. First channel member 111 includes a first end 111a and a second end 111b. Second channel member 112 includes a first end 112a and a second end 112b. A lumen or passageway 114 extends from first end 111a to second end 111b of the first channel member, and from first end 112a to second end 112b of the second channel member. A sidewall 115 helps define the lumen or passageway of each channel member.

A pair of posts 117a and 117b extend radially inward from sidewall 115 at one end of each channel member. The ends having the posts 117a and 117b are pivotally connected, such as with interlocking teeth 119 and hinge 120. The posts are located at a position such that the distance between the posts corresponds to the distance between two central apertures in a prosthetic disc nucleus, such as the disc nucleus shown in FIGS. 16–18, when the disc nucleus is in its relaxed configuration.

A locking mechanism 125 is preferably included as part of instrument 110. Locking mechanism 125 may include a locking arm 126 and a locking pin 127. Locking arm 126 may be hinged, such as with hinge 128. Locking pin 127 may be moved by pin lever 129, which operates to push locking pin 127 over locking arm 126, or to pull locking pin 127 away from locking arm 126. Locking arm 126 may include indents to facilitate positioning locking arm 126 over posts 117a and 117b when locking arm 126 is in its locked position. Alternative and/or additional locking mechanisms may be provided, with the purpose of the mechanism being to hold the instrument in its straightened (implantable) configuration.

One channel member (for example, channel member 111) preferably has a dilator 140 at its distal end. The primary purpose of the dilator is to dilate a small opening in a disc annulus so that a larger-sized implant can be passed through the hole.

Dilator 140 may include one or more arms 141 and 142 sized to dilate a hole in a disc annulus. In some embodiments one of the arms is shorter, and one of the arms is longer. This provides several advantages, as described below.

First, having arms with differing lengths may allow the instrument to be used where the hole in the annulus is too small to accommodate both arms until some initial dilation is begun. When the tip of the longer arm is inserted into the annulus hole first, the hole can initially be dilated by twisting the instrument 90°. Then, after the hole has been initially dilated, the shorter arm of the dilator can be inserted and used to complete the dilation.

Second, having arms with differing lengths allows one arm to provide stability to the implant as the implant is being inserted, while not interfering with the folding of the implant as the implant enters the disc nucleus space. For example, as shown in FIG. 3 below, the longer arm supports the outer surface of the implant as the implant is being delivered, thus directing the implant into the disc nucleus space at the appropriate orientation. At the same time, the shorter arm is clear of the implant in the direction in which the implant is folding, thus allowing the implant to fold more efficiently upon insertion into the disc space.

As can be appreciated by persons skilled in the art, and as described more fully below, alternative and/or additional dilators may be provided to dilate the portal in the annulus. Such dilators may also facilitate positioning and folding of a prosthetic disc nucleus, as generally described herein.

A plunger mechanism 150 may be provided to cooperate with the channel member that does not include a dilator. In one preferred embodiment plunger mechanism 150 includes a shaft 151 having a plunger 152 at one end. Teeth 154 on shaft 151 are used to advance shaft 151 when lever arm 153 is pulled. A knob 155 at the proximal end of shaft 151 may be used to manipulate the mechanism.

Figure 12:
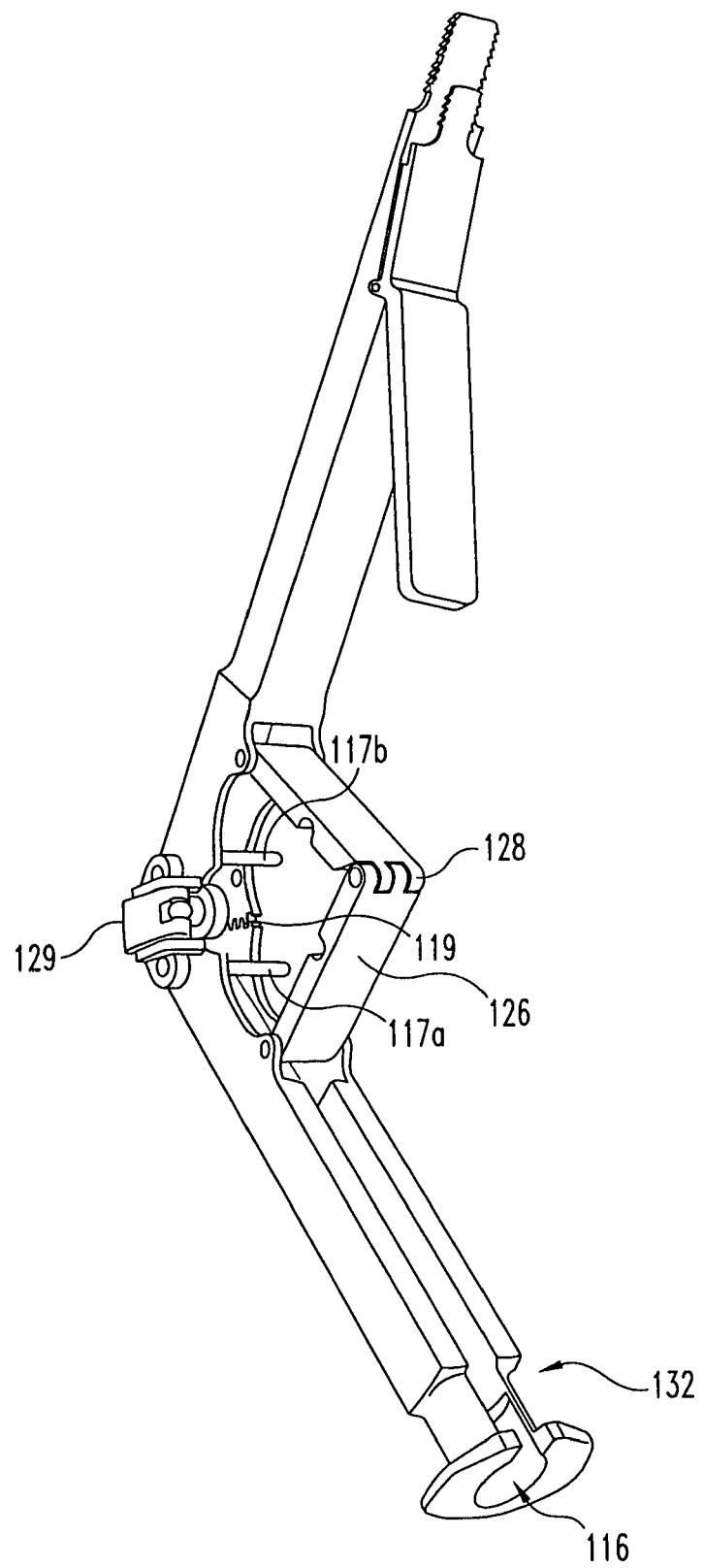
FIG. 12 is a perspective view of one preferred embodiment of a disc nucleus delivery instrument, with the instrument in its loading configuration.
Figure 13:
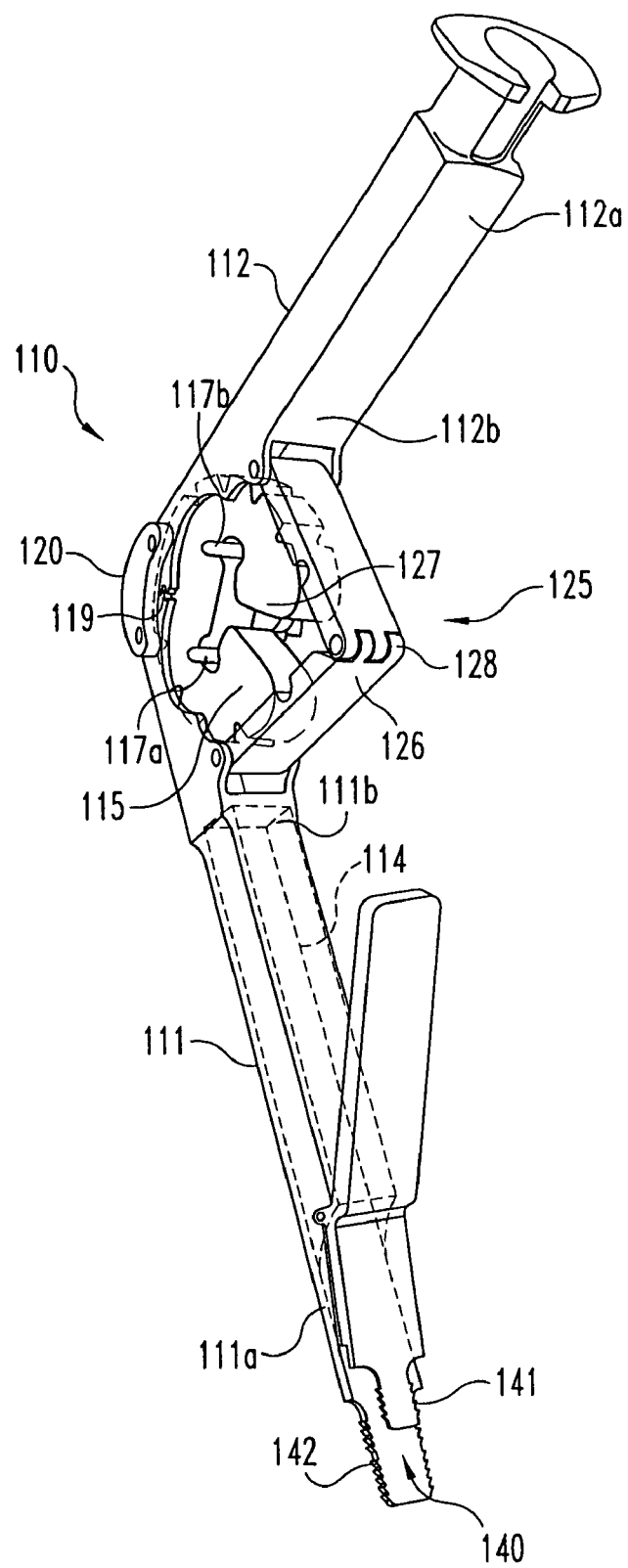
FIG. 13 is another perspective view of the disc nucleus delivery instrument of FIG. 12.

To further describe additional aspects of the disc delivery instrument described above, it is to be appreciated that when the spinal disc implant delivery device is in a loading configuration (i.e., a configuration where the first channel member and the second channel member form an angle of about 90°, as shown in FIGS. 11–13), a spinal disc implant can easily be loaded into the device by placing a spinal disc implant into the device such that it is held in position by the posts. When the first channel member and the second channel member are moved in opposing directions as shown in FIG. 13, the device is converted from its loading configuration to its implantable configuration (i.e., a configuration where the first channel member and the second channel member form an angle of about 180°, as shown in FIG. 14).

In devices lacking a dilator at the distal end of the delivering channel member, the implantable configuration is also the deliverable configuration (i.e., a configuration where the first channel member and the second channel member form an angle of about 180°, and the instrument is ready to deliver the disc nucleus material). However, in devices which comprise a dilator, the arms of the dilator are typically "closed" when the device is in its implantable configuration. To convert the instrument to its deliverable configuration, the dilator must be activated so that the distance between the first arm and second arm increases. This design allows for the dilator arms to extend into the disc space of a patient's spine in its implantable configuration and then to dilate an opening in the annulus of the disc upon conversion to its deliverable configuration.

It is also to be appreciated that the activation of the dilator can either be "active" (i.e., controlled by the surgeon without passing the implant through the dilator, such as by a lever as shown in FIGS. 11–14) or "passive" (controlled by passage of the implant through the dilator). When the conversion is active, the device may further comprise a means for performing such conversion. Any means capable of doing such a conversion is contemplated in the invention. For example, the device can comprise a twisting mechanism wherein the clockwise and counter-clockwise movement of this mechanism controls the up and down or otherwise retractable movement of the first arm and/or second arm. Such movement will either increase or decrease the distance between the two arms, thus converting the device back and forth between the implantable configuration and deliverable configuration. A passive conversion will involve an increase in the distance between the first arm and second arm by the movement of the spinal disc implant through the arms and into the disc space.

Figure 14:
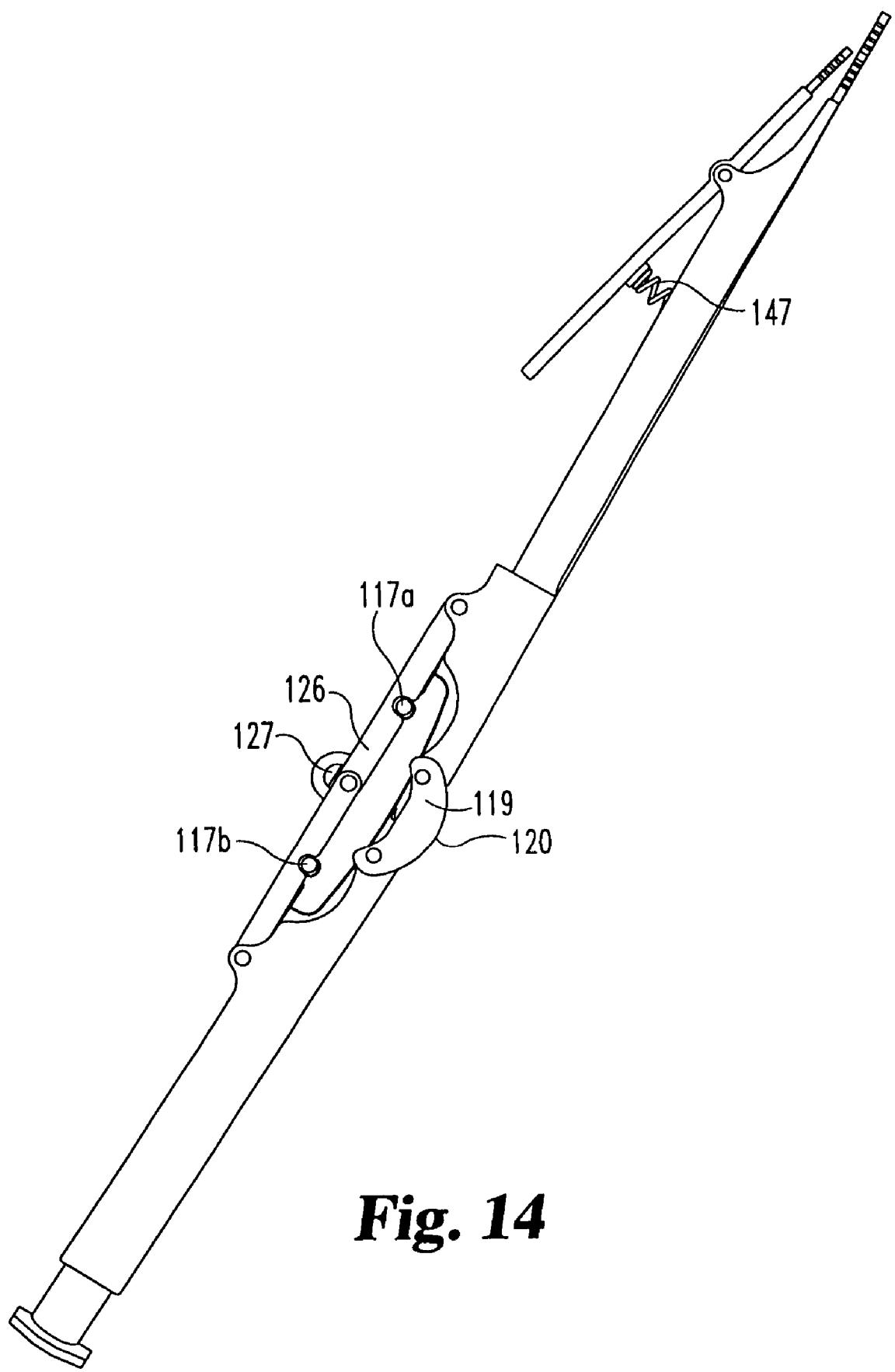
FIG. 14 shows the disc nucleus delivery instrument of FIG. 12 in its delivering configuration.
Figure 15:
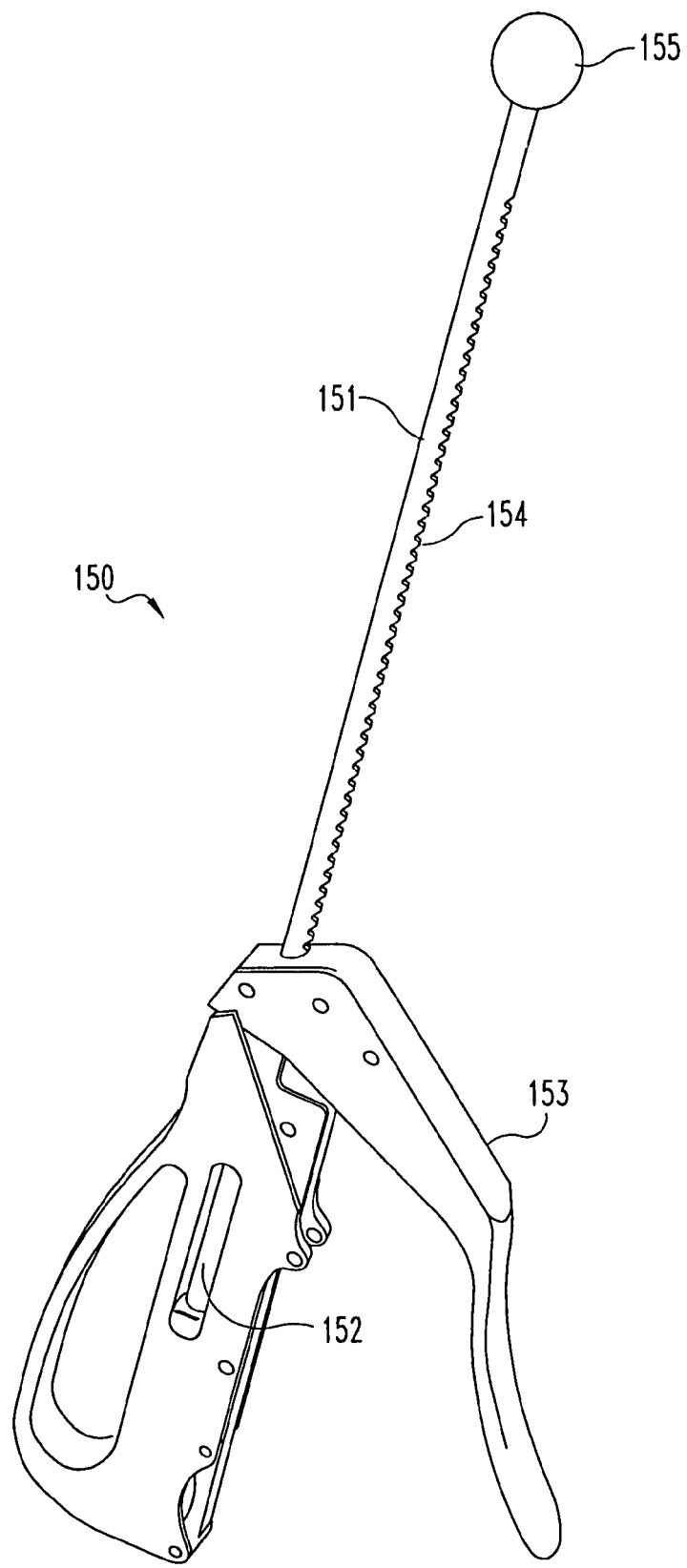
FIG. 15 shows one preferred embodiment of a plunger device useful with the disc nucleus delivery instrument of FIG. 12.

When the device is in its implantable or deliverable configuration, the device is substantially straight, as shown in FIG. 14. To maintain that configuration, the device may comprise a means for locking the device in this configuration, as previously indicated. For example, the device can contain a movable extension located in the loading area of the device. The movable extension is controlled by a releasing mechanism, wherein when the movable middle joint is brought just above the locking mechanism, the movable middle joint becomes substantially straight and is locked in place by the locking mechanism. The releasing mechanism, once activated, will release the movable middle joint from the locking mechanism; thereby converting the device back to its loading configuration.

Figure 16:
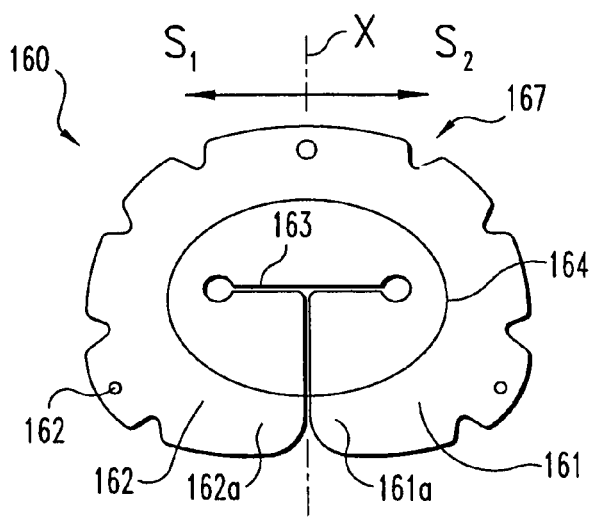
FIG. 16 shows one preferred embodiment of a disc nucleus implant that may be implanted with the disc nucleus delivery instrument of FIG. 12 according to one aspect of the present invention.
Figure 17:
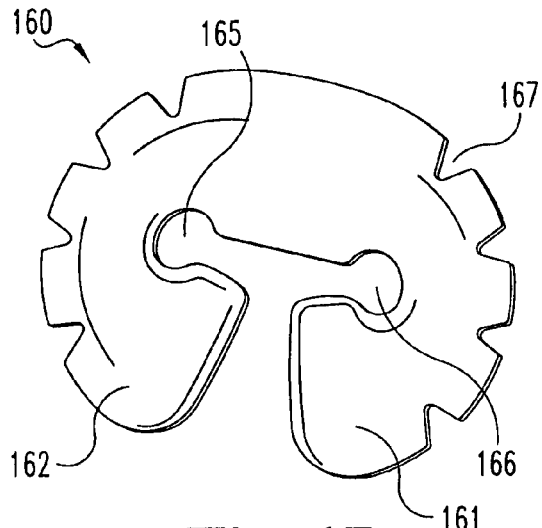
FIG. 17 shows the disc nucleus implant of FIG. 17 in a partially straightened configuration.
Figure 18:
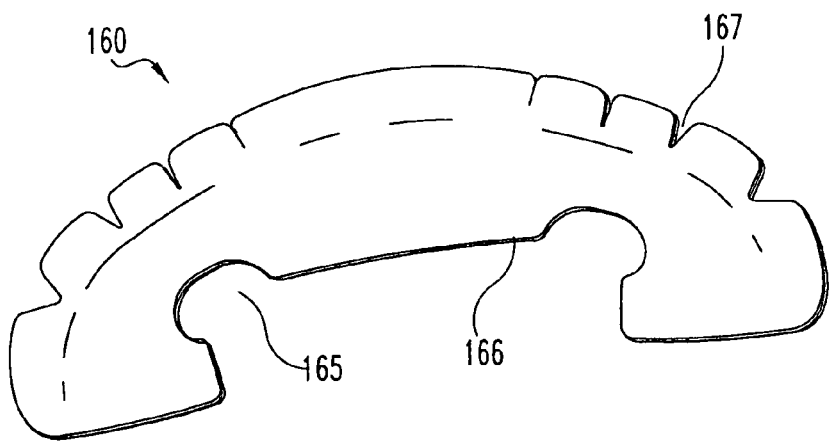
FIG. 18 shows the disc nucleus implant of FIG. 17 in a nearly straightened configuration.

As to the disc nucleus materials that may be implanted using the inventive instruments and methods described herein, FIGS. 16–18 shows one preferred embodiment of a disc nucleus implant that may be implanted with disc delivery instrument 110. Implant 160 comprises a pair of arms 161 and 162 that are folded to form an inner fold 163 when the implant is in its relaxed configuration. The folded arms abut one another at their ends 161a and 162a when the implant is relaxed, so that the center core 164 of the implant (when viewed from above as in FIG. 16) is substantially solid.

Apertures 165 and 166 are provided to correspond to posts 117a and 117b of the disc delivery instrument. When the posts are inserted into the apertures and the hinged channel members are pivoted to an angle of about 180°, implant 160 straightens to provide a cross sectional size that is less than the cross sectional size of the folded implant. Grooves 167 are provided on the outer surface to prevent cracking or tearing of the implant when the implant is in its straightened configuration. X-ray markers such as tantalum markers 168 may be included to assist in positioning the implant. Preferably, a larger x-ray marker is provided in the anterior portion of the implant, and smaller x-ray markers are provided in posterior portions of the implant.

It is to be appreciated that the inventive methods disclosed herein may be used when the surgical approach is posterior, anterior, lateral, or oblique. To illustrate those alternatives, FIGS. 19–24 show anterior approaches, in contrast to the posterior approaches shown in FIGS. 1–10.

Figure 19:
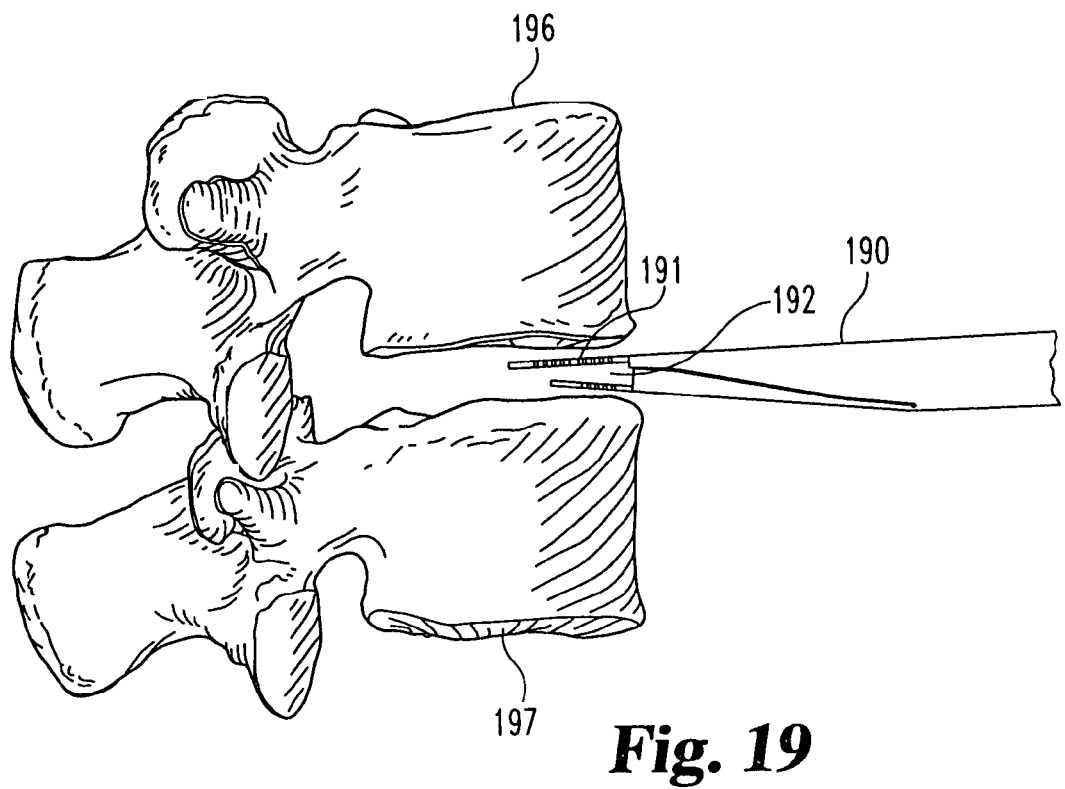
FIG. 19 shows a disc delivery instrument being inserted between two vertebrae prior to implantation of a disc nucleus material.
Figure 20:
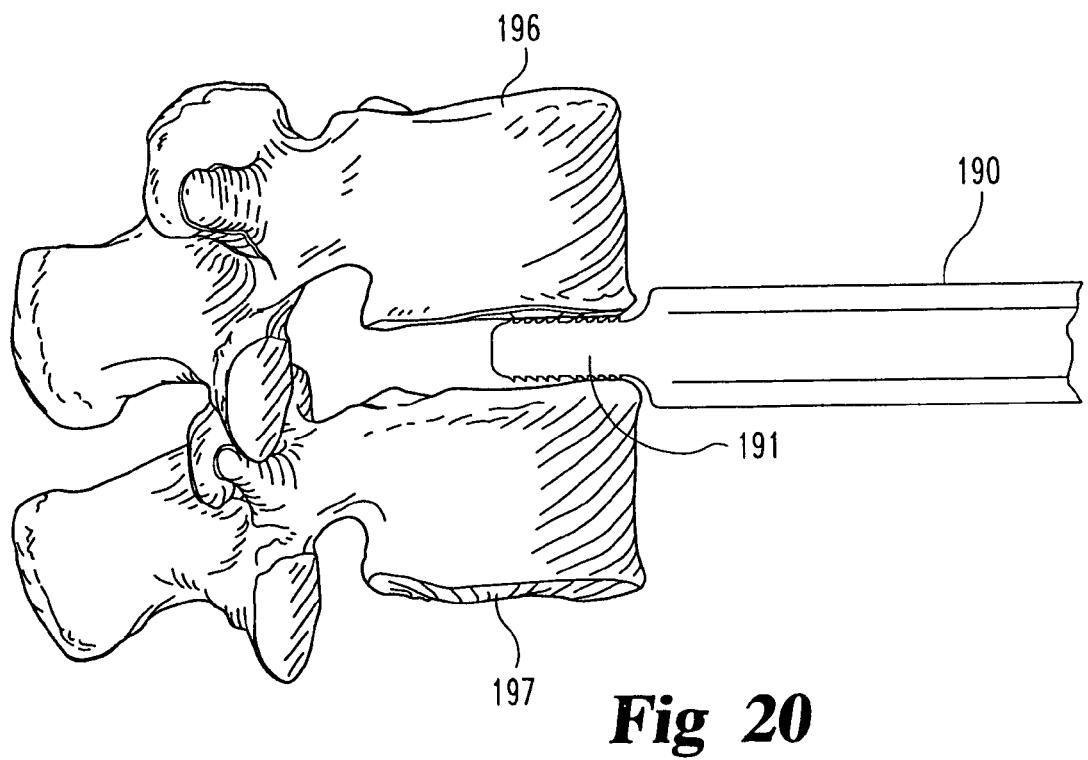
FIG. 20 shows a disc delivery instrument being rotated 90° between two vertebrae to facilitate separation of the vertebra and implantation of a disc nucleus material.

In FIGS. 19 and 20, a disc nucleus delivery instrument 190 is inserted between adjacent vertebrae 196 and 197. The instrument is inserted so that at least one of the dilation arms 191 and 192 is generally parallel to the intervertebral space, as shown in the Figures. Preferably, the instrument is inserted so that the adjacent vertebrae are not distracted by the insertion of the instrument. Most preferably, the instrument does not even contact the adjacent vertebral end plates when the instrument is inserted. Then, the device is rotated 90° so that said at least one of the dilation arms is generally perpendicular to the intervertebral space. When the distance D1 between the two vertebrae is smaller than the width W1 of at least one of the dilation arms, rotating the instrument causes the vertebrae to distract, providing more space for the disc nucleus implant. Accordingly, distance D2 in FIG. 20 is greater than distance D1 in FIG. 19.

Figure 21:
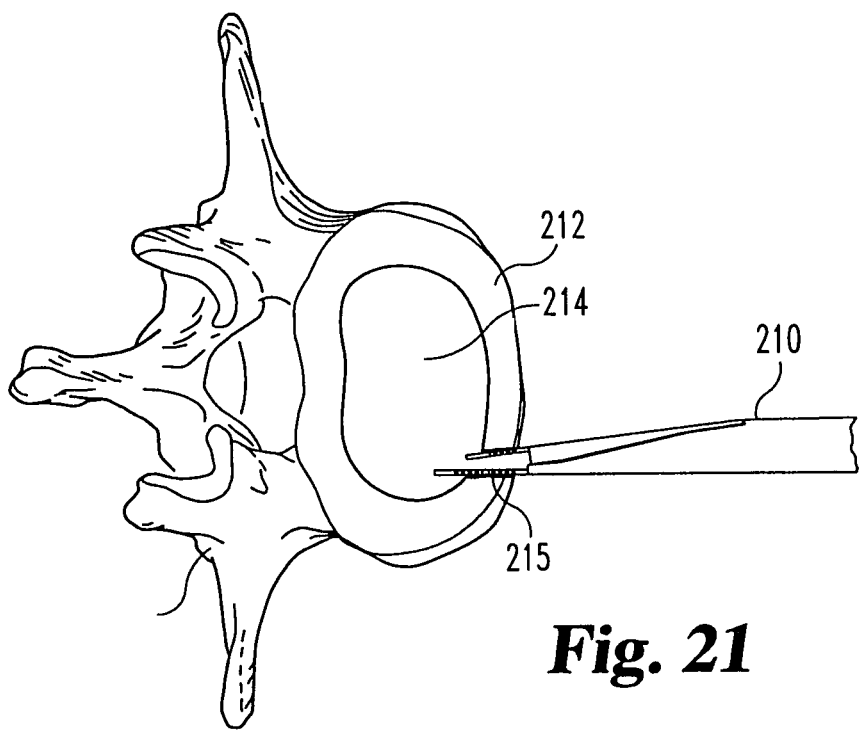
FIG. 21 shows an aspect of the present invention wherein the disc delivery instrument has been inserted into a disc annulus from an anterior approach, and is ready to dilate the annulus hole.
Figure 22:
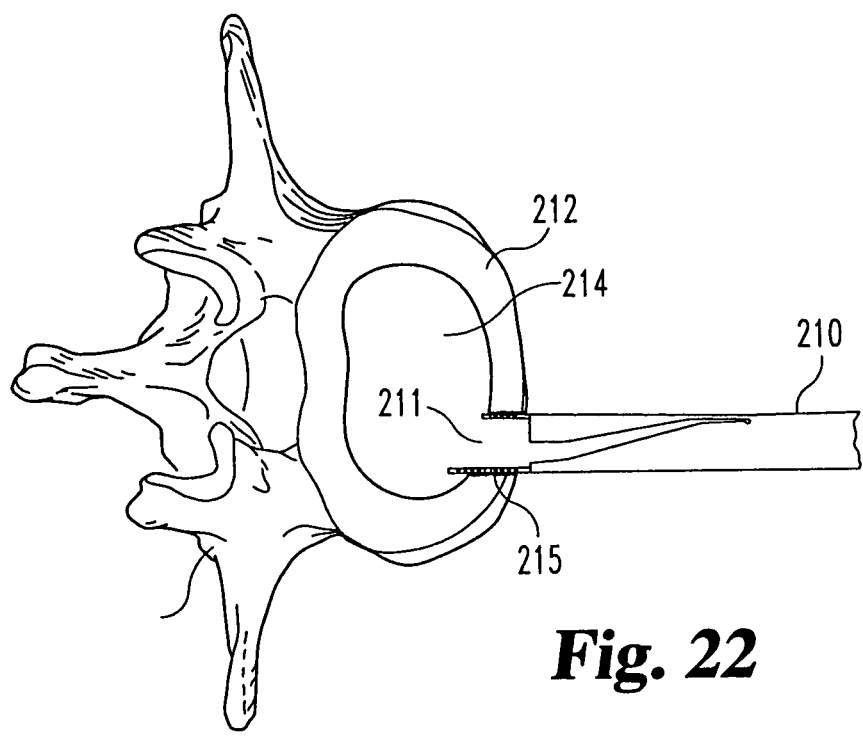
FIG. 22 shows the approach illustrated in FIG. 21, wherein the disc delivery instrument has dilated the annulus hole.

In FIG. 21 a disc nucleus delivery instrument 210 is inserted into a hole 211 in annulus 212. Dilator 215 of instrument 210 is used to dilate hole 211 so that a disc nucleus material may be implanted in disc nucleus space 214. Accordingly, opening or hole 211 is larger when dilated, as shown in FIG. 22, than when undilated, as shown in FIG. 21.

Figure 23:
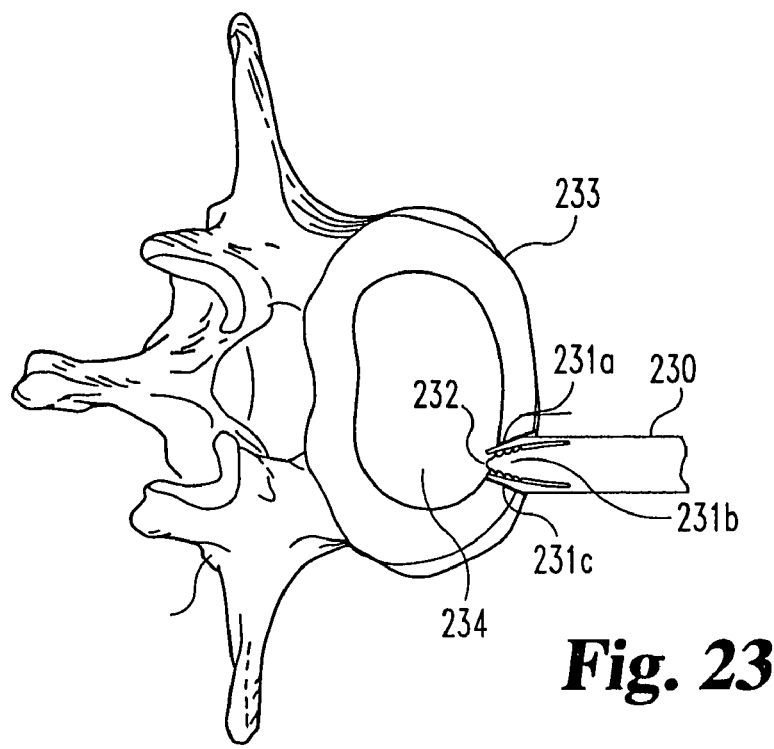
FIG. 23 shows another embodiment of a disc delivery instrument being inserted into a disc annulus from an anterior approach, with the dilator of the disc delivery instrument comprises a multiplicity of arms.
Figure 24:
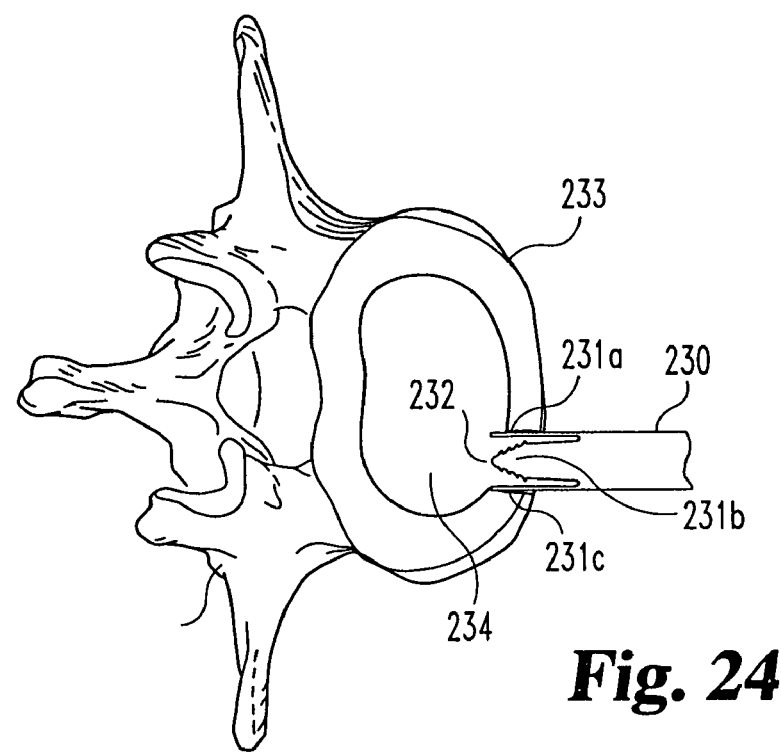
FIG. 24 shows the embodiment of FIG. 23 after the disc delivery instrument has dilated the annulus hole.

In FIGS. 23 and 24, an instrument having a dilator comprising more than two arms is illustrated. Instrument 230 includes dilator 231 having arms 231a, 231b, 231c, and 231d (not shown). As with previous embodiments, dilator 231 is inserted into disc annulus 232 and is activated to dilate the annulus opening. A disc nucleus device can then be implanted into disc nucleus space 234 to repair or replace a defective disc nucleus.

Figure 25:
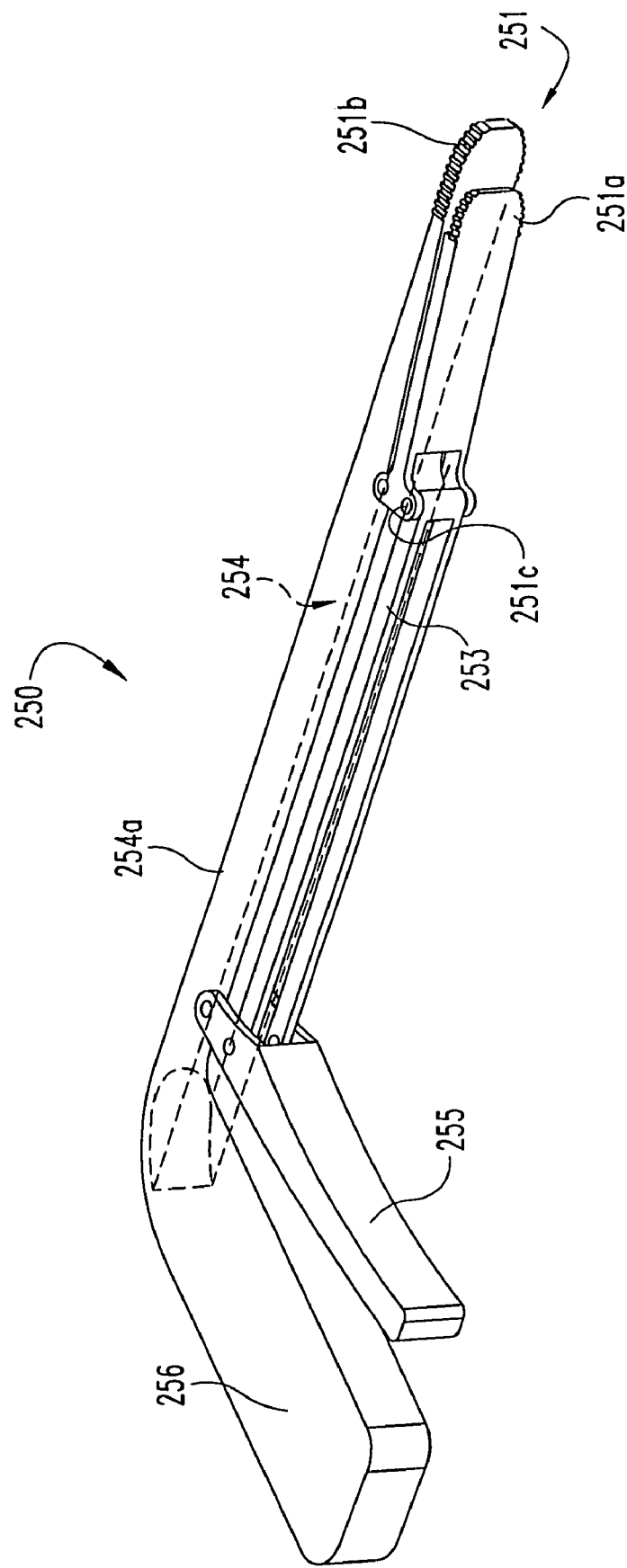
FIG. 25 shows another embodiment of a disc delivery instrument according to the present invention.
Figure 26:
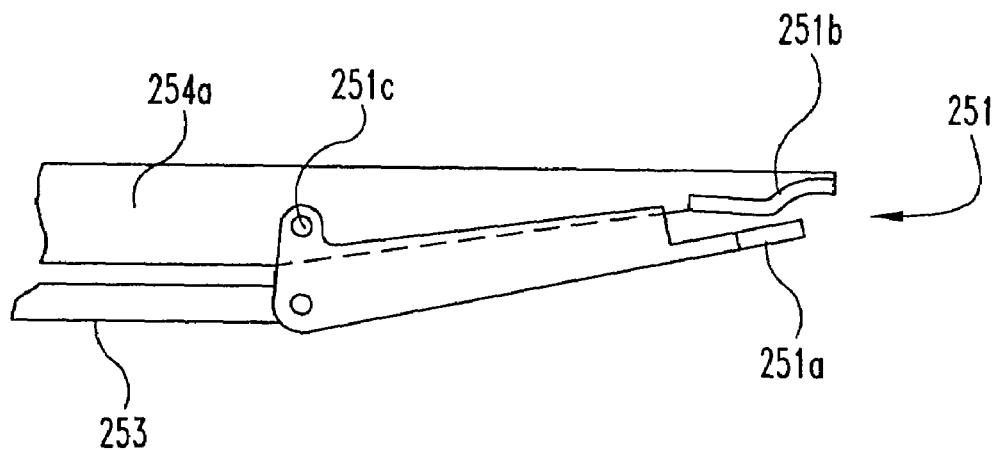
FIG. 26 shows the disc delivery instrument of FIG. 25, with the dilator in its closed configuration.
Figure 27:
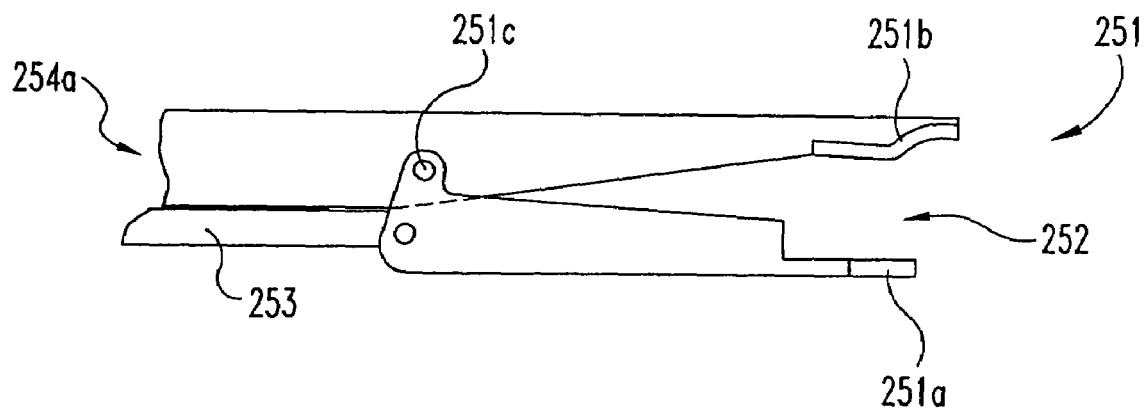
FIG. 27 shows the disc delivery instrument of FIG. 25, with the dilator in its open, dilating configuration.

FIGS. 25–27 show another embodiment of a disc nucleus delivery instrument. Instrument 250 includes a channel member 254 having a dilator 251 at one end. Dilator 251 includes dilator arms 251a and 251b, with dilator arm 251a being attached to arm 251b with pin 251c. Arm 251a is also attached to activator handle 255 by activator arm 253. When activator handle 255 is pulled toward grip 256, activator arm 253 pivots arm 251a on pin 251c, thereby dilating dilator 251 as shown in the drawings.

Figure 28:
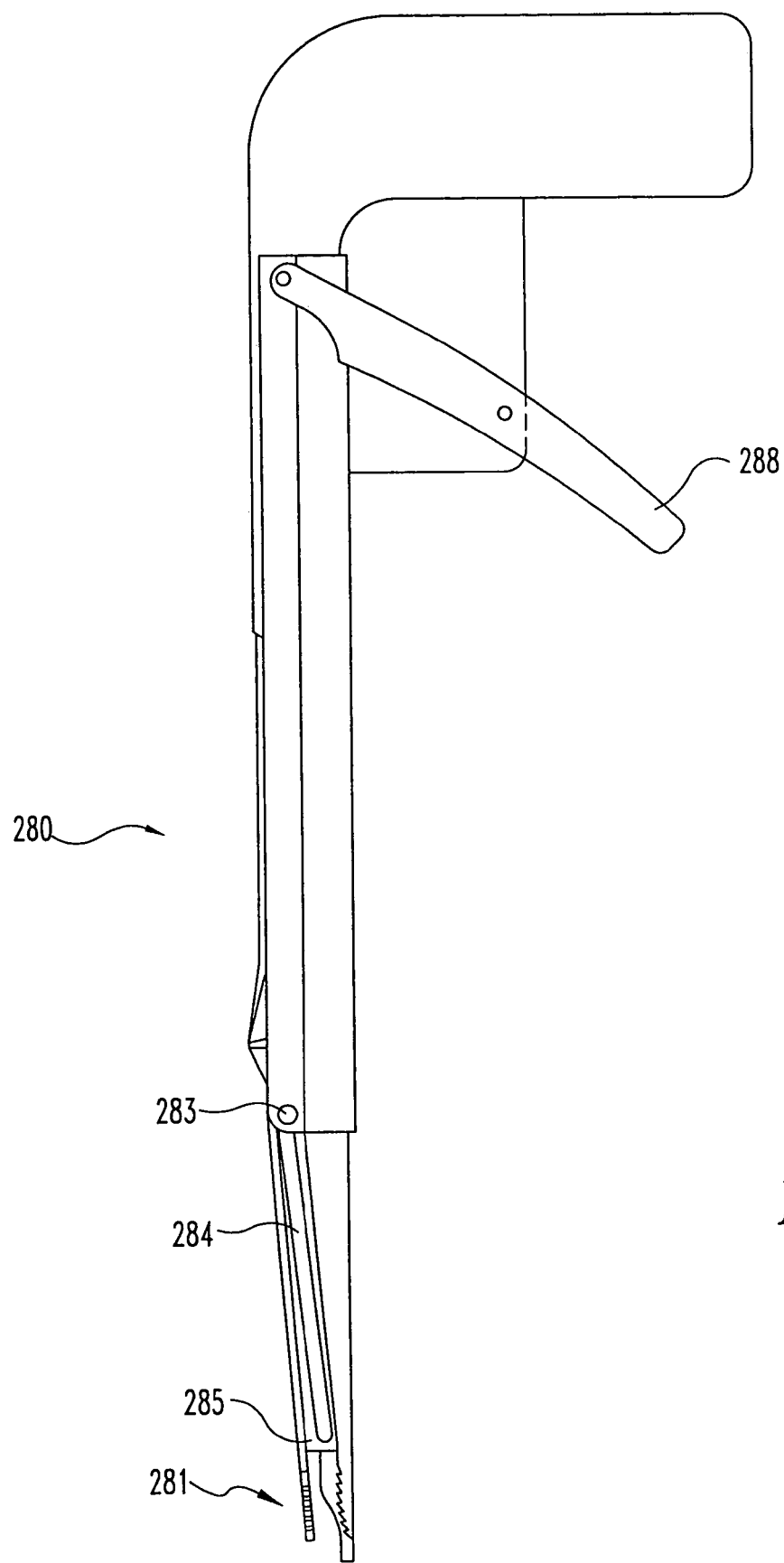
FIG. 28 shows another embodiment of a disc delivery instrument according to the present invention, with the dilator in its closed configuration.
Figure 29:
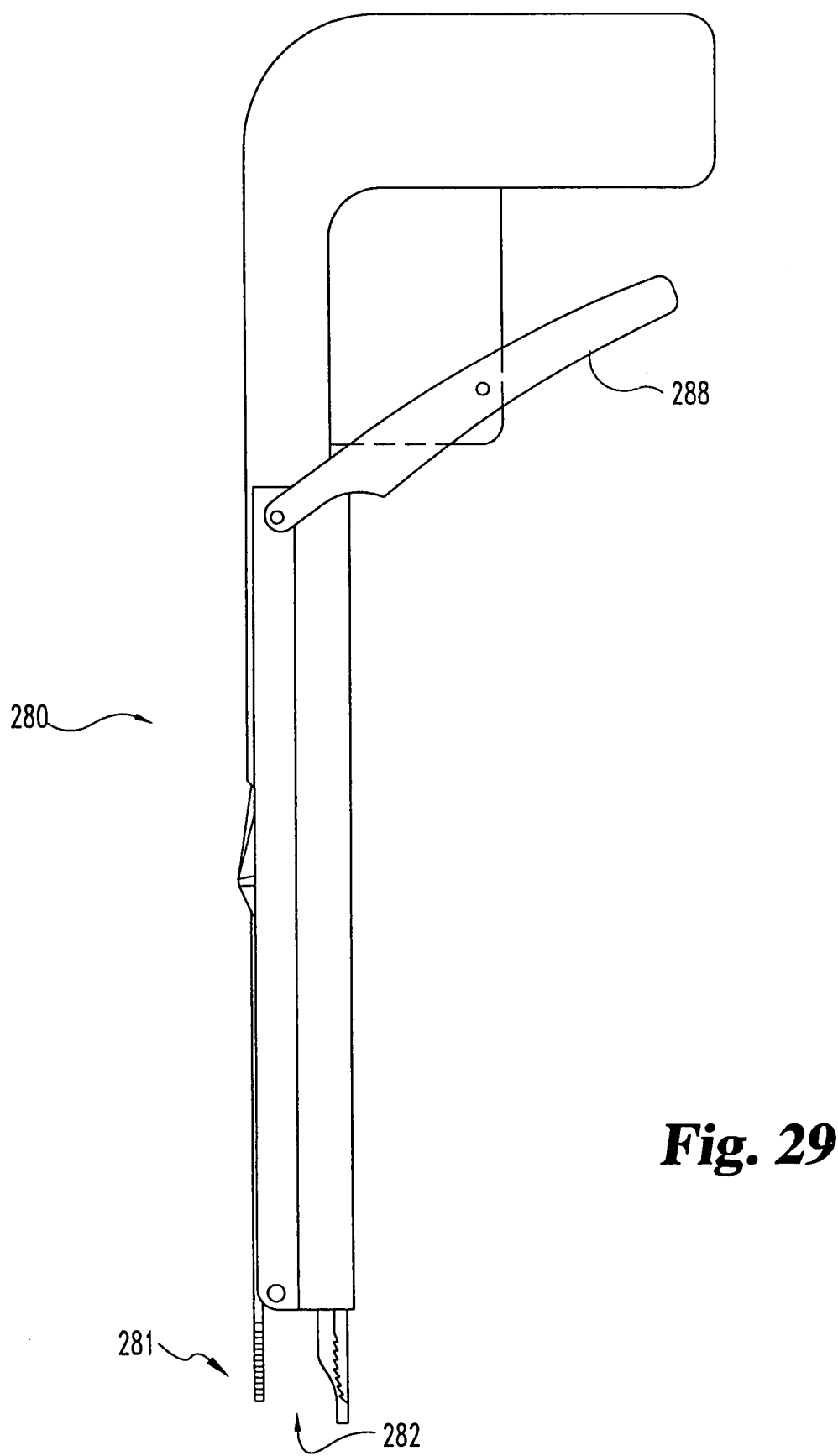
FIG. 29 shows the disc delivery instrument of FIG. 28, with the dilator in its open, dilating configuration.

FIGS. 28–29 show an alternative embodiment of an instrument for delivering a disc nucleus replacement device. In FIG. 28 instrument 280 comprises a dilator 281 at the end of a channel member 282. Dilator 281 is activated by pushing pin 283 through groove 284 in arm 285. Handle 288 may be used to activate the dilator. When handle 288 is advanced, pin 283 raises arm 285, thus dilating dilator 281.

Figure 30:
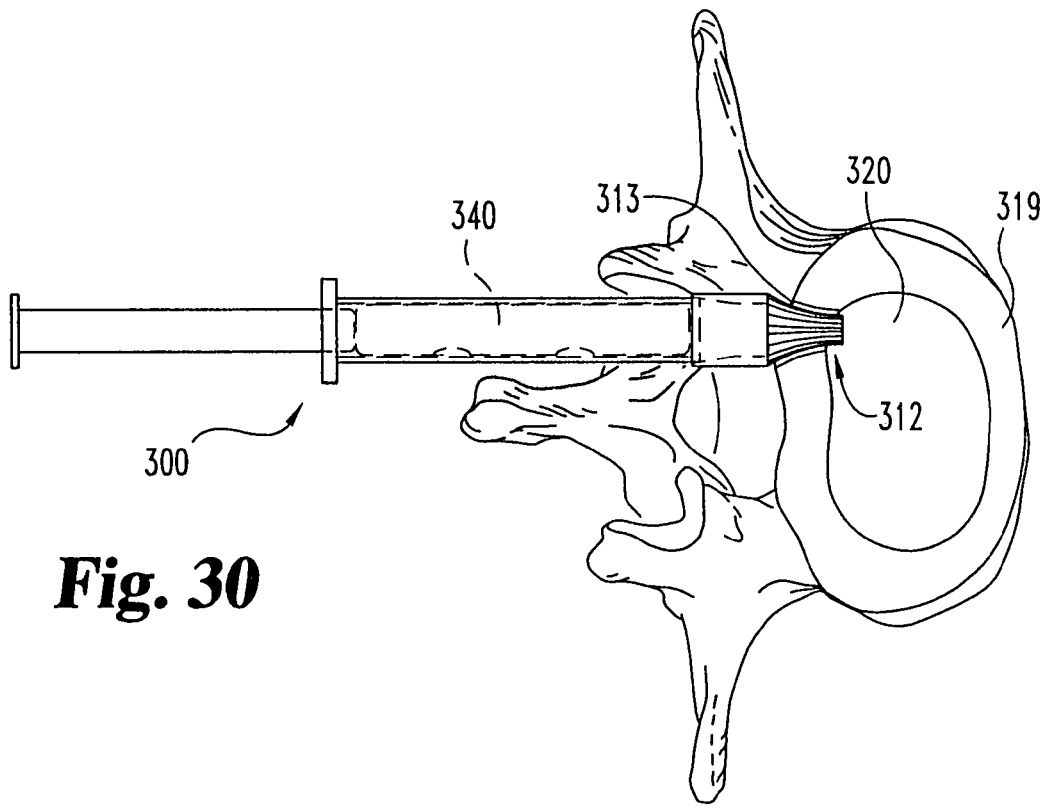
FIG. 30 shows an embodiment of the present invention wherein the disc delivery instrument has a dilator that does not include an activator, wherein the instrument contains a straightened disc nucleus material and has been inserted into a disc annulus and is ready to dilate the annulus hole.

FIGS. 30–34 show a "passive" instrument for delivering a disc nucleus replacement device. In FIG. 30, instrument 300 has been pushed through an opening 313 in disc annulus 319 so that the end of the instrument is positioned in disc nucleus space 320. Dilator 312, which comprises a multiplicity of arms 318, is in its undilated (closed) position. Implant 340 resides in the instrument channel member.

Figure 31:
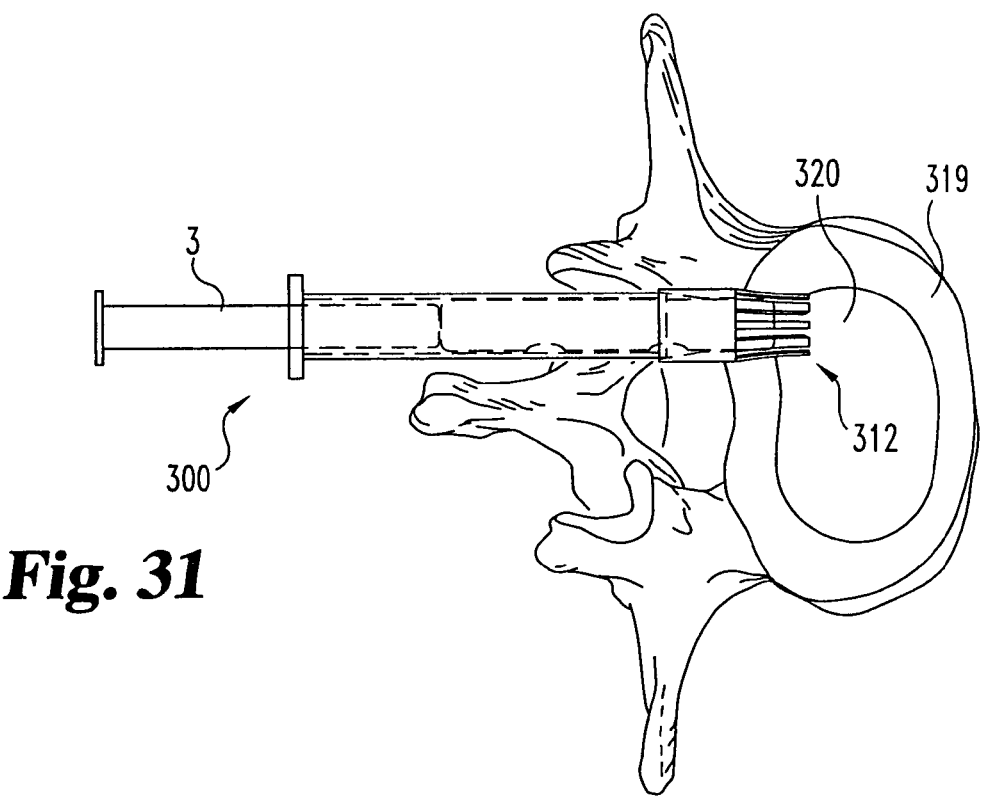
FIG. 31 shows the embodiment of FIG. 30 wherein the disc delivery instrument has been inserted into a disc annulus and has dilated the annulus hole.

In FIG. 31, implant 340 is being pushed through dilator arms 318, causing dilator 312 and annulus opening 313 to dilate.

Figure 32:
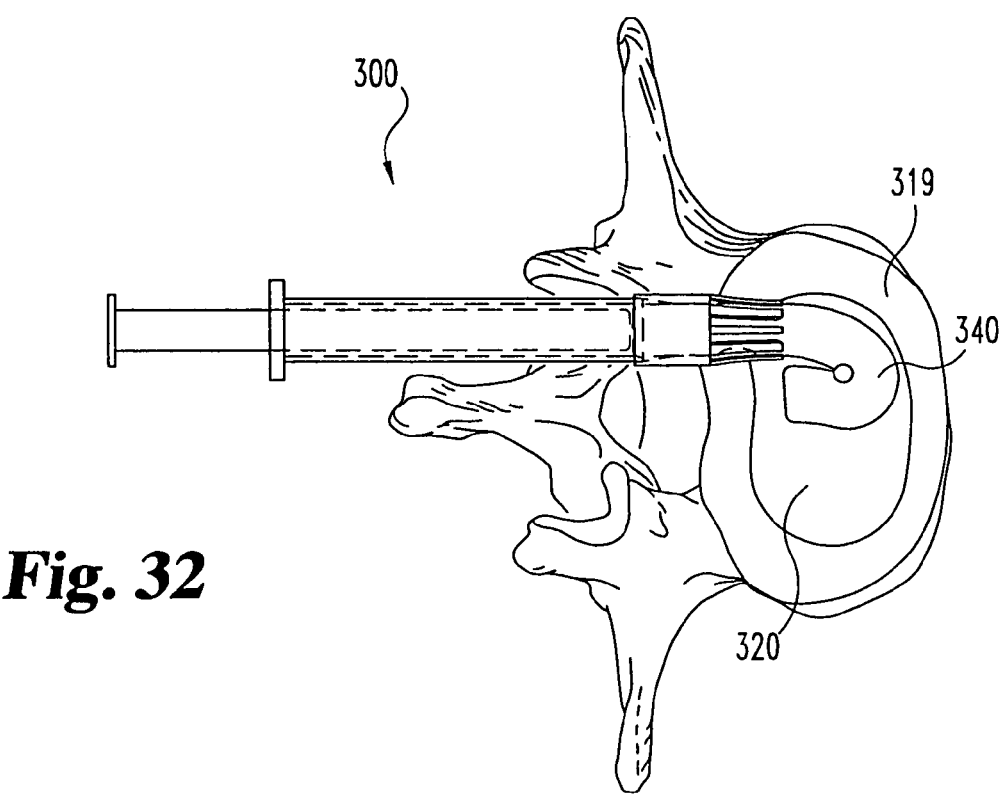
FIG. 32 shows the embodiment of FIG. 30 wherein a disc nucleus material is being delivered into a disc nucleus space through the dilated annulus hole.
Figure 33:
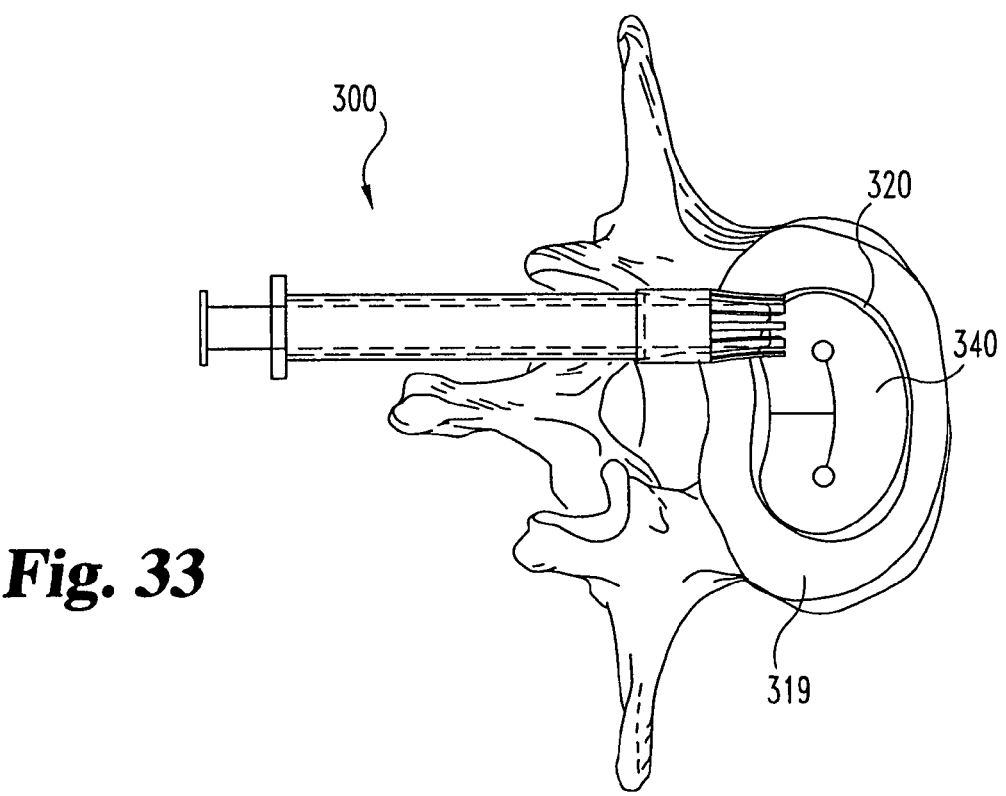
FIG. 33 shows the embodiment of FIG. 30 wherein a disc nucleus material has been delivered into a disc nucleus space through the dilated annulus hole.
Figure 34:
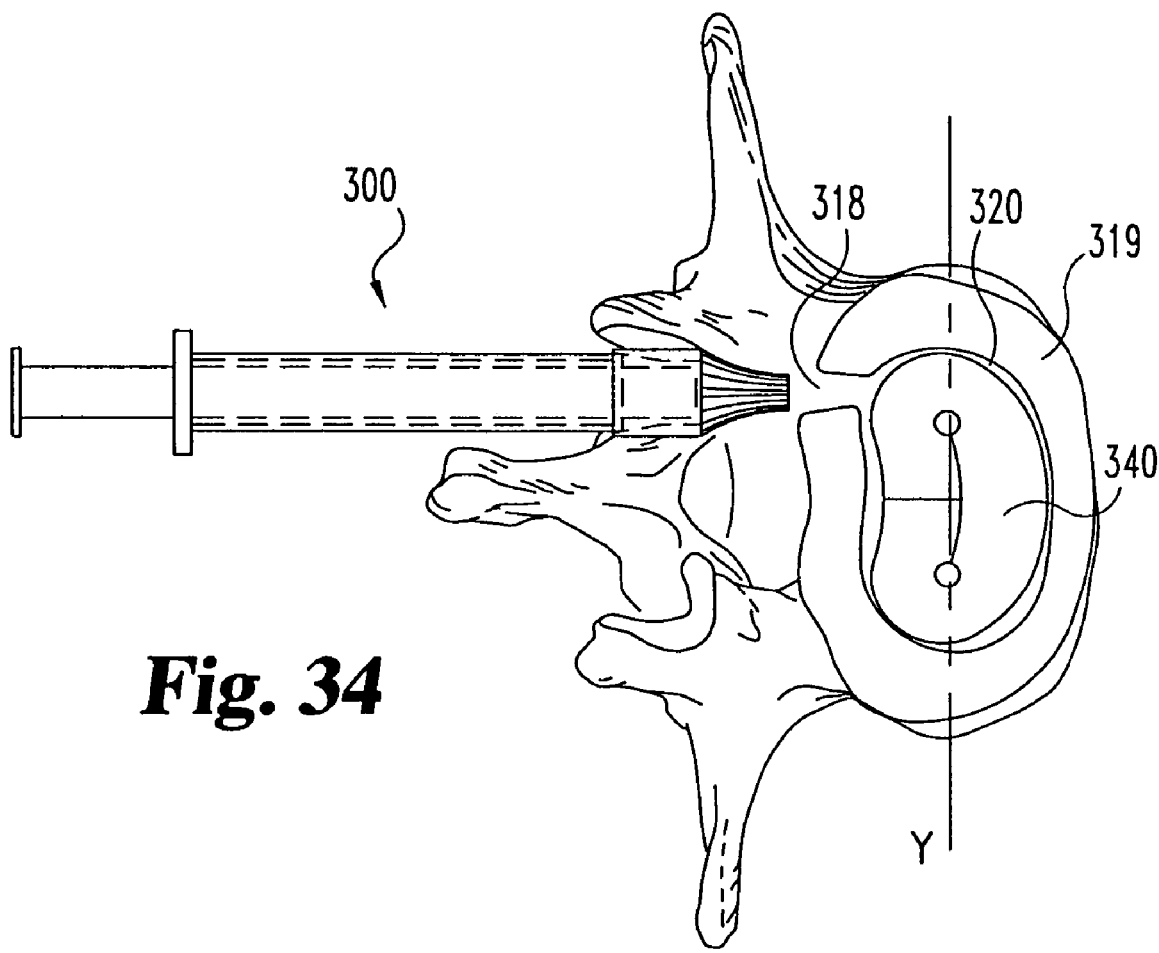
FIG. 34 shows the embodiment of FIG. 30 wherein the disc delivery instrument has been withdrawn from the disc annulus hole, and the implanted disc nucleus material has assumed its relaxed configuration.

In FIG. 32, implant 340 is being pushed into disc nucleus space 320. Since in the illustrated embodiment implant 340 has a shape memory that causes it to assume a folded configuration, when implant 340 enters disc nucleus space 320 it begins folding to that folded configuration. After the implant has been delivered, dilator 312 returns to its undilated (closed) configuration, and instrument 300 is withdrawn from the annulus opening.

The spinal disc implant delivery device and instrument described herein may be made from a variety of materials, including metals known to the art, such as stainless steel and titanium alloys, polymers known to the art, including polyethylene, polypropylene, polyetheretherketone and polyacetal.

EXAMPLE 1

A medical patient is treated to replace a damaged or degenerated lumbar intervertebral disc nucleus using the procedure described below.

A/P and M/L radiographs are obtained to determine the size and shape of the affected level. The largest implant that can be accommodated by patient anatomy without overdistraction is selected, choosing among implants having footprints of 19 mm×23 mm to 22 mm×27 mm, and a height of between 6 mm and 14 mm. It is important to select the tallest device that can be accommodated by the interbody space. Excessive annulus laxity may cause non-central seating of the implant. X-ray templates are used to determine whether a small or large device footprint should be used, as are AP and ML implant outlines to determine the appropriate height.

The patient is placed in a direct prone positioned on the operating table. Bolster appropriately to maintain lumbar lordosis. C-arm fluoroscopy is not absolutely necessary for the procedure, but is preferred if available. Intraoperative imaging is useful for evaluation of the nucleus cavity preparation, as well as for adjusting and confirming device orientation.

A 5 cm incision is made in the midline directly over the posterior spinous processes. The skin incision is sharply carried down through subcutaneous tissues to the dorsal lumbar fascia. Great care is taken to preserve the midline ligamentous structures. A longitudinal incision is made in the dorsal lumbar fascia 5 mm lateral to the posterior spinous processes. The multifidus is subperiostally elevated off of the posterior spinous processes and adjacent lamina. Great care is taken to protect and preserve the facet joint capsule and joint.

A high speed burr is used to create a small laminotomy window. The ligamentum flavum is sharply incised and removed. A Kerrison rongeur is used to enlarge the laminotomy site if necessary. The traversing nerve root is identified and gently retracted medially.

Epidural veins are coagulated using bipolar electrocautery. The posterior annulus is identified. A working portal through the annulus is created following insertion of the trephine device.

Preservation of the annulus fibrosis minimizes the risk of implant expulsion. A progressive dilation technique is employed to gain access to the nucleus pulposus. If properly dilated and protected, the viscoelastic annulus fibers should relax postoperatively, leaving only a small defect.

A starting hole is created in the annulus using a 3 mm trephine. The first dilator is then inserted, taking care not to damage the anterior margin of the annulus (FIG. 3). Larger dilators are then provided over each shaft in sequence until the desired access is achieved.

A variety of tools are used to properly clear the nucleus cavity, including specialized pituitary rongeurs and curettes for reaching the contralateral margin of the nucleus pulposus. Ring curettes are used to scrape adhesions from the vertebral endplates if necessary. Care is taken to thoroughly prepare the cavity such that it is centralized, symmetrical, and large enough to accept the desired implant footprint. Care is taken to avoid damaging the annulus fibrosis.

The endplate jack is inserted into the intervertebral space and is actuated until moderate distraction is achieved. Care is taken to avoid overdistraction. The position is maintained for approximately 60 seconds to allow the annulus fibers to relax, adjusting if necessary during the process. The height on the jack scale is identified and the corresponding implant is selected. When the desired implant falls between sizes, a smaller implant size is selected.

An instrument set containing numerous device inserter bodies, with internal geometry specific to corresponding implants, is used to insert the implant. All inserter bodies interface with a common ratchet assembly and push rod. The inserter body is chosen to correspond to the correct implant size and the implant is installed in the instrument. The instrument is then fully straightened to its deliverable configuration.

The inserter functions much like a caulking gun. The loaded inserter body is assembled with the ratchet handle, and the push rod is positioned into the ratchet handle until it touches the nucleus replacement device. Care is taken to assure that the ratchet teeth are on the correct side. The ratchet handle is then actuated to advance the implant to a position just before the shorter foot of the inserter pivot. This minimizes the time and travel required for insertion once the instrument is installed at the operative site. If an implant is accidentally advanced to the point where the shorter foot begins to open, the implant is extruded out of the device and the inserter is reloaded. The push rod is rotated 180-degrees to release the mechanism The inserter tips are placed in the annular opening prior to extruding the nucleus replacement device beyond the pivot point of the shorter foot. The inserter is then positioned such that the stationary portion is lateral and the pivoting shorter foot is medial. This allows the implant to curl into the prepared space as it is extruded out of the inserter. As the nucleus replacement device fills the nucleus cavity, it will tend to push the inserter out of the disc space. Moderate axial force is applied during the final stage of extrusion to counter this effect. If the trailing edge of the Nucleus Replacement Device protrudes slightly from the annulus following insertion, it can be easily pushed into closed position.

Under fluoroscopic control, final position of the Nucleus Replacement Device is adjusted using tamps provided in the instrument set. Correct positioning is verified by inspection of the radiographic markers imbedded in the device. Positioning verification is facilitated by the fact that the anterior marker is slightly larger than the two posterior markers. When correctly placed, three collinear markers are visible in the frontal plane, with the central marker being larger than the outer two. In the sagittal plane, a larger anterior marker and two closely positioned posterior markers is visible.

While the invention has been illustrated and described in detail in the drawings and foregoing description, the same is to be considered as illustrative and not restrictive in character, it being understood that only the most preferred embodiments have been shown and described, and that all changes and modifications that come within the spirit of the invention are desired to be protected. In addition, all publications cited herein are indicative of the abilities of those of ordinary skill in the art and are hereby incorporated by reference in their entirety as if individually incorporated by reference and fully set forth.

What is claimed is:

1. A method of implanting material in an intervertebral disc nucleus space; the method comprising:
   (a) providing a disc nucleus implant instrument having:
      (i) a passageway effective for passing a material for replacing or augmenting an intervertebral disc nucleus, said passageway having a proximal end and a distal end; and
      (ii) a dilator at the distal end of said passageway, said dilator being effective for dilating an opening in a disc annulus;
   (b) providing a material suitable for replacing or augmenting an intervertebral disc nucleus in the passageway of said disc nucleus implant instrument;
   (c) providing a hole in the annulus of a disc receiving the material for replacing or augmenting an intervertebral disc nucleus, said hole having an undilated size that is smaller than the cross-sectional size of the material for replacing or augmenting an intervertebral disc nucleus, and said hole having a dilated size that is larger than the cross-sectional size of the material for replacing or augmenting an intervertebral disc nucleus;
   (d) introducing the dilator of said disc nucleus implant instrument into the hole in the disc annulus while said hole is not fully dilated;
   (e) causing said dilator to dilate, and thus to dilate the hole in the disc annulus;
   (f) passing said material for replacing or augmenting an intervertebral disc nucleus through said dilator and into said disc nucleus space while the hole in said disc annulus is dilated; and
   (g) withdrawing said disc nucleus implant instrument and allowing said hole in said disc annulus to return to a size smaller than its dilated size.

2. The method of claim 1 wherein said dilator comprises at least two arms for dilating a hole in a disc annulus.

3. The method of claim 2 wherein at least one of said at least two arms is fixed with respect to said passageway for passing a prosthetic disc nucleus.

4. The method of claim 2 wherein at least two of said at least two arms are movable with respect to said passageway for passing a prosthetic disc nucleus.

5. The method of claim 2 wherein said disc nucleus implant instrument further includes an activator for causing the dilator to dilate; and wherein the method further includes the step of activating the activator to move at least one of said at least two arms to dilate a hole in a disc annulus.

6. The method of claim 5 wherein at least one of said at least two arms is fixed with respect to said passageway for passing a prosthetic disc nucleus.

7. The method of claim 5 wherein at least two of said at least two arms are movable with respect to said passageway for passing a prosthetic disc nucleus.

8. The method of claim 5 wherein said activator includes a lever for activating said dilator and for causing at least one of said at least two arms to move and to dilate a hole in a disc annulus.

9. The method of claim 5 wherein said activator includes an inclined plane for activating said dilator and for causing at least one of said at least two arms to move and to dilate a hole in a disc annulus.

10. The method of claim 5 wherein said activator includes a screw for activating said dilator and for causing at least one of said at least two arms to move and to dilate a hole in a disc annulus.

11. The method of claim 1 wherein said disc nucleus implant instrument further includes an activator for causing the dilator to dilate; and wherein the method further includes the step of activating the activator to dilate the dilator.

12. The method of claim 11 wherein said activator includes a lever for activating said dilator.

13. The method of claim 11 wherein said activator includes an inclined plane for activating said dilator.

14. The method of claim 11 wherein said activator includes a screw for activating said dilator.

15. The method of claim 1 wherein said disc nucleus implant instrument further includes a locking mechanism for holding said dilator in a dilating position.

16. A method of implanting a prosthetic spinal disc nucleus in an intervertebral disc nucleus space; the method comprising:
   (a) providing a disc nucleus implant instrument having:
      (i) a passageway for passing a prosthetic disc nucleus, said passageway having a proximal end and a distal end; and
      (ii) a dilator at the distal end of said passageway, said dilator being effective for dilating an opening in a disc annulus;
   (b) providing a prosthetic disc nucleus having a first configuration and a second configuration, wherein said first configuration presents a first cross-sectional size and said second configuration presents a second cross-sectional size, wherein said first cross-sectional size is larger than said second cross-sectional size;
   (c) providing a hole in the annulus of a disc receiving the prosthetic disc nucleus, said hole having an undilated size that is smaller than the first cross-sectional size of said prosthetic disc nucleus, and said hole having a dilated size that is larger than the second cross-sectional size of said prosthetic disc nucleus;
   (d) providing said prosthetic disc nucleus in its second configuration in the passageway of said disc nucleus implant instrument;
   (e) introducing the dilator of said disc nucleus implant instrument into the hole in the disc annulus while said hole is not fully dilated;
   (f) causing said dilator to dilate, and thus to more fully dilate the hole in the disc annulus;

(g) passing said prosthetic disc nucleus through said dilator and into said disc nucleus space while the disc annulus is more fully dilated and the prosthetic disc nucleus is in its second configuration;

(h) withdrawing said disc nucleus implant instrument and allowing said disc annulus to return to a size smaller than its dilated size;

(i) causing or allowing said prosthetic disc nucleus to assume its first configuration.

17. The method of claim 16 wherein said disc nucleus implant instrument further includes an activator for causing the dilator to dilate; and wherein the method further includes the step of activating the activator to dilate the dilator.

18. The method of claim 17 wherein said activator includes a lever for activating said dilator.

19. The method of claim 17 wherein said activator includes an inclined plane for activating said dilator.

20. The method of claim 17 wherein said activator includes a screw for activating said dilator.

21. The method of claim 16 wherein said dilator comprises at least two arms for dilating a hole in a disc annulus.

22. The method of claim 21 wherein said disc nucleus implant instrument further includes an activator for causing the dilator to dilate; and wherein the method further includes the step of activating the activator to move at least one of said at least two arms to dilate a hole in a disc annulus.

23. The method of claim 22 wherein said activator includes a lever for activating said dilator and for causing at least one of said at least two arms to move and to dilate a hole in a disc annulus.

24. The method of claim 22 wherein said activator includes an inclined plane for activating said dilator and for causing at least one of said at least two arms to move and to dilate a hole in a disc annulus.

25. The method of claim 22 wherein said activator includes a screw for activating said dilator and for causing at least one of said at least two arms to move and to dilate a hole in a disc annulus.

26. The method of claim 22 wherein at least one of said at least two arms is fixed with respect to said passageway for passing a prosthetic disc nucleus.

27. The method of claim 22 wherein at least two of said at least two arms are movable with respect to said passageway for passing a prosthetic disc nucleus.

28. The method of claim 16 wherein said disc nucleus implant instrument further includes a locking mechanism for holding said dilator in a dilating position.

29. The method of claim 16 wherein said prosthetic disc nucleus comprises a load bearing elastic body having shape memory and sized for placement into an intervertebral disc space, said body having a first end, a second end, and a central portion; wherein said shape memory biases said body to a first configuration wherein said first end and said second end are positioned adjacent to said central portion to form at least one inner fold and to provide a substantially solid center core when the implant is in its first configuration; said elastic body configurable into a second, straightened configuration for insertion through an opening in an intervertebral disc annulus fibrosis; wherein said shape memory returns said body to said first configuration after said insertion.

30. The method of claim 16 wherein said prosthetic disc nucleus comprises a load bearing elastic body sized for placement into an intervertebral disc space, said body having a first end, a second end, a central portion, and a first configuration wherein said first end and said second end are positioned adjacent to said central portion to form at least one inner fold, said elastic body configurable into a second, straightened configuration for insertion through an opening in an intervertebral disc annulus fibrosis, said body configurable back into said first configuration after said insertion; wherein said elastic body has a surface that includes wrinkles, indents or projections that relieve stress and prevent cracking or tearing of the implant when the implant is straightened for implantation.

31. A device for implanting a prosthetic spinal disc nucleus, comprising:

(a) a first channel member having a first end and a second end, said first channel member defining a channel from said first end to said second end, said channel comprising at least one side wall;

(b) a post extending radially inward from said first channel member side wall, said post being located near the first end of said first channel member;

(c) a second channel member having a first end and a second end, said second channel member defining a channel from said first end to said second end, said channel comprising at least one side wall;

(d) a post extending radially inward from said second channel member side wall, said post being located near the first end of said second channel member; wherein said first channel member and said second channel member are pivotally connected at their respective first ends;

wherein the device assumes a loading configuration when the first channel member and the second channel member are pivotally connected to define an angle of less than 180 degrees; and wherein the device assumes an implanting configuration when the first channel member and the second channel member are pivotally connected to define an angle of approximately 180 degrees.

32. The device of claim 31 and further including a locking mechanism to lock the device into its implanting configuration.

33. The device of claim 31 wherein the second end of said first channel member terminates in a tip compressible to a cross section smaller than the cross section of the first end of said first channel member.

34. The device of claim 33 wherein said tip comprises at least two arms.

35. The device of claim 34 wherein at least one of said at least two arms includes teeth.

36. The device of claim 34 wherein at least one of said at least two arms is rigid, and at least one of said at least two arms is flexible.

37. The device of claim 33 wherein said tip comprises a pair of opposing arms.

38. The device of claim 37 wherein at least one of said pair of opposing arms is shorter than the other of said pair of opposing arms.

* * * * *